(12) United States Patent
Nataro et al.

(10) Patent No.: US 8,906,662 B2
(45) Date of Patent: Dec. 9, 2014

(54) COMPOSITIONS AND METHODS FOR TREATING INFLAMMATORY BOWEL DISEASE AND AIRWAY INFLAMMATION

(75) Inventors: James Nataro, Charlottesville, VA (US); Fernando Ruiz-Perez, Charlottesville, VA (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 13/516,234

(22) PCT Filed: Dec. 22, 2010

(86) PCT No.: PCT/US2010/061758
§ 371 (c)(1),
(2), (4) Date: Jul. 11, 2012

(87) PCT Pub. No.: WO2011/087835
PCT Pub. Date: Jul. 21, 2011

(65) Prior Publication Data
US 2013/0017173 A1    Jan. 17, 2013

Related U.S. Application Data

(60) Provisional application No. 61/289,005, filed on Dec. 22, 2009.

(51) Int. Cl.
| | |
|---|---|
| *C12N 9/52* | (2006.01) |
| *C11D 3/386* | (2006.01) |
| *A61K 38/16* | (2006.01) |
| *A61K 35/00* | (2006.01) |
| *A61K 38/48* | (2006.01) |

(52) U.S. Cl.
CPC .............. *A61K 38/164* (2013.01); *C11D 3/386* (2013.01); *A61K 2035/11* (2013.01); *C12N 9/52* (2013.01); *A61K 38/482* (2013.01)
USPC ......................... 435/220; 424/93.1; 424/94.64

(58) Field of Classification Search
None
See application file for complete search history.

(56) References Cited

U.S. PATENT DOCUMENTS

2009/0305267 A1* 12/2009 Krause et al. ................... 435/6

OTHER PUBLICATIONS

Henderson et al., Infection and Immunity, vol. 67, No. 11, p. 5587-5596, 1999.*
Henderson IR et al. (2001). Virulence Functions of Autotransporter Proteins. Infection and Immunity, v69(3), p. 1231-1243.*
Dutta PR et al. (2002). Functional Comparison of Serine Protease Autotransporters of Enterobacteriaceae. Infection and Immunity, v70(12), p. 7105-7113.*
Bellini EM et al. (2005). Antibody response against plasmid-encoded toxin (Pet) and the protein involved in intestinal colonization (Pic) in children with diarrhea produced by enteroaggregative *Escherichia coli*. FEMS Immunology and Medical Microbiology, v43, p. 259-264.*
Harrington SM et al. (2009). The Pic Protease of Enteroaggregative *Escherichia coli* promotes intestinal colonization and growth in the presence of mucin. Infection and Immunity, v77(6), p. 2465-2473.*
Sturm A et al. (2004). Divergent cell cycle kinetics underlie the distinct functional capacity of mucosal T cells in Crohn's disease and ulcerative colitis. Gut, v53, p. 1624-1631.*
Navarro-Garcia F et al. (2010). Pic, an Autotransporter protein secreted by different pathogens in the Enterobacteriaceae family, is a potent mucus secretagogue. Infection and Immunity, v78(10), p. 4101-4109.*
de Souza HL et al. (2013). Mucosa-associated but not luminal *Escherichia coli* is augmented in Crohn's disease and ulcerative colitis. Gut Pathogens, v4(21), p. 1-8.*
ISR and Written Opinion in related PCT matter PCT/US2010/061758.
IPRP in related PCT matter PCT/US2010/061758.
Ian Henderson et al., "Characterization of Pic, a secreted protease of *Shigella flexneri* and enteroaggregative *Escherichia coli*." Infection and Immunity, 67(11): 5587-5596 (1999).
Maria Kostakioti et al., "Functional analysis of the Tsh autotransporter from an avian pathogenic *Escherichia coli* strain." Infection and Immunity, 72(10):5548-5554 (2004).
Ian Henderson et al. "Virulence functions of autotransporter proteins." Infection and Immunity, 69(3): 1231-1243 (2001) see abstract; table 1; p. 1235, right-hand column.
Susan Turner et al., "Weapons of mass destruction: virulence factors of the global killer enterotoxigenic *Escherichia coli*.," FEMS Microbiol. Lett., 263: 10-20 (2006) see abstract; p. 16.
Al-Hasani, Keith et al., "The Immunogenic SigA Enterotoxin of *Shigella flexneri* 2a Binds to HEp-2 Cells and Induces Fodrin Redistribution in Intoxicated Epithelial Cells", PLoS One, 2009 vol. 4(12), e8223.
Canizalez-Roman, Adrian et al., "Fodrin CaM-binding domain cleavage by Pet from enteroaggregative *Escherichia coli* leads to actin cytoskeletal disruption", Mol Microbiol 2003 vol. 48(4) pp. 947-958.
Dutta, Pinaki et al., "Functional Comparison of Serine Protease Autotransporters of Enterobacteriaceae", Infection Immunity 2002 vol. 70(12) pp. 7105-7113.

(Continued)

*Primary Examiner* — Cherie M Stanfield
*Assistant Examiner* — Sean C Barron
(74) *Attorney, Agent, or Firm* — Kristina Castellano; Castellano PLLC

(57) ABSTRACT

Provided are compositions and methods for treating inflammation due to an immune response. Non-limiting example compositions include class-2 SPATE proteins that are capable of cleaving proteins involved in an inflammatory immune response in a patient. Example compositions include at least one mucin-cleaving class-2 SPATE protein. Further example compositions include protein involved in intestinal colonization (Pic). Non-limiting example methods include methods of decreasing inflammation in a patient having inflammation and methods of perturbing immune response in a patient having a disease or condition in which an active immune response is attributable to a cause of the disease or condition, by administering to the patient a composition including at least one class-2 SPATE protein capable of cleaving proteins involved in an inflammatory immune response.

10 Claims, 34 Drawing Sheets

(56) References Cited

OTHER PUBLICATIONS

Harrington, Susan et al., "The Pic Protease of Enteroaggregative *Escherichia coli* Promotes Intestinal Colonization and Growth in the Presence of Mucin", Infection Immunity 2009 vol. 77 (6) pp. 2465-2473.

Navarro-Garcia, Fernando et al., "Plasmid-Encoded Toxin of Enteroaggregative *Escherichia coli* is Internalized by Epithelial Cells", Infection & Immunity 2001, vol. 69(2),pp. 1053-1060.

Navarro-Garcia, Fernando et al., "Pic, an Autotransporter Protein Secreted by Different Pathogens in the Enterobacteriaceae Family, Is a Potent Mucus Secretagogue," Infection & Immunity 2010, vol. 78(10),pp. 4101-4109.

* cited by examiner

Neutrophils

| | |
|---|---|
| Mucin | PKY$^{337}$ - S$^{338}$ ETN |
| CD44 | RSS$^{188}$ - T$^{189}$ SGG |
| CD44 | PWI$^{212}$ - T$^{213}$ DST |
| PSGL-1 | EAL$^{262}$ - S$^{263}$ TEP |
| PSGL-1 | ALS$^{263}$ - T$^{264}$ EPS |
| CD45 | NAI$^{143}$ - S$^{144}$ DVP |
| CD45 | AVI$^{212}$ - S$^{213}$ TTT |

(Aliphatic/small aa.) (Aliphatic/small aa.) – cleavage - (S/T with potential O-linked oligosaccharide)

FIG. 13C

COMPOSITIONS AND METHODS FOR TREATING INFLAMMATORY BOWEL DISEASE AND AIRWAY INFLAMMATION

RELATED APPLICATIONS APPLICATION

This application is a U.S. National Stage Application of PCT/US2010/061758 filed on Dec. 22, 2010, which claims the benefit of U.S. Provisional Application No. 61/289,005, filed on Dec. 22, 2009, the contents of each of which are hereby incorporated herein by reference in their entirety.

STATEMENT OF FEDERALLY SPONSORED RESEARCH AND DEVELOPMENT

This invention was made with government support under Grant Numbers AI043615 and AI033096 awarded by the National Institutes of Health. The government has certain rights in the invention.

TECHNICAL FIELD

The present invention relates to compositions and methods of treating inflammatory diseases, including inflammatory bowel disease, airway inflammation, cancer, and other inflammatory disorders, and methods for carrying out the methods.

BACKGROUND OF INVENTION

Inflammatory Bowel Disease

The term inflammatory bowel disease ("IBD") describes a group of chronic inflammatory disorders of unknown causes in which the intestine (bowel) becomes inflamed, often causing recurring cramps or diarrhea. IBD is generally divided into ulcerative colitis (UC) and Crohn's disease. In UC, the inflammatory response is confined to the mucosa and submucosa of the colon with clear demarcations. In Crohn's disease, the entire gastrointestinal tract can be involved and the inflammation can extend through the intestinal wall from mucosa to serosa. Areas of inflammation may be interspersed with relatively normal mucosa. In Crohn's disease, the predominant symptoms are diarrhea, abdominal pain and weight loss whereas in UC diarrhea is the main symptom, often accompanied by rectal bleeding. Both diseases are common in the industrialized world, with highest incidences in North America and Northern Europe (Russel et al., Scand J Gastroenterol 1996; 31: 417-27). In a European study, the average annual incidence was 5.9/100,000 for Crohn's disease and 11.2/100,000 for UC (Shivananda et al., Gut 1996; 39: 690-7). The peak age of onset for both diseases is between 15 and 30 years with a second minor peak between 55 and 80 years. Crohn's disease shows a higher incidence in females than in males. UC seems more equally distributed between the sexes, with a tendency to a male preponderance.

Clinically, IBD is characterized by diverse manifestations often resulting in a chronic, unpredictable course. Bloody diarrhea and abdominal pain are often accompanied by fever and weight loss. Anemia is not uncommon, as is severe fatigue. Joint manifestations ranging from arthralgia to acute arthritis as well as abnormalities in liver function are commonly associated with IBD. Patients with IBD also have an increased risk of colon carcinomas compared to the general population. During acute "attacks" of IBD, work and other normal activity are usually impossible, and often a patient is hospitalized. A detailed description of IBD symptoms and sequelae is found in, for example, Northfield, Drugs, Vol. 14, pages 198-206 (1977); Blaker et al, Eur. J. Pediatr., Vol. 139, pages 162-164 (1982); Singleton, The Gastroenterology Annual, pages 268-310 (1983); Saco et al, J. Amer. Acad. Dermatol., Vol. 4, pages 619-629 (1981); Prantera et al, Ital. J. Gastroenterol., Vol. 13, pages 24-27 (1981); Sales et al, Arch. Int. Med., Vol. 143, pages 294-299 (1983); and Ament, Inflammatory Bowel Diseases, Martinus Nijhoff Publ., Boston, Mass., pages 254-268 (1982).

Although the cause of IBD remains unknown, several factors such as genetic, infectious, and immunologic susceptibility have been implicated. IBD is much more common in Caucasians, especially those of Jewish descent. The chronic inflammatory nature of the condition has prompted an intense search for a possible infectious cause. Although agents have been found which stimulate acute inflammation, none has been found to cause the chronic inflammation associated with IBD. The hypothesis that IBD is an autoimmune disease is supported by the previously mentioned extraintestinal manifestation of IBD as joint arthritis, and the known positive response to IBD by treatment with therapeutic agents such as adrenal glucocorticoids, cyclosporine and azathioprine, which are known to suppress immune responses. In addition, the GI tract more than any other organ of the body, is continuously exposed to potential antigenic substances such as proteins from food, bacterial byproducts (LPS), etc.

Diarrheal diseases remain a major global health problem, particularly among children under 5 years of age. Among the most important pathogens causing diarrhea are *Shigella* spp and diarrheagenic *E. coli* pathotypes (Moore S R *Curr Opin Gastroenterol*, Kaper J B, Nataro J P, & Mobley H L (2004) *Nat Rev Microbiol* 2, 123-140. 3. O'Ryan M, Prado V, & Pickering L K (2005) *Semin Pediatr Infect Dis* 16, 125-136). In aggregate, these pathogens are estimated to cause more than 1 million deaths per year. Despite their importance as agents of human disease, there remain many unanswered questions regarding the pathogenetic mechanisms of these microorganisms, and there are no licensed vaccines for any of these agents. One potential obstacle to the use of attenuated pathogens as enteric vaccines is the possibility that they may exhibit as yet undiscovered mechanisms of immune suppression.

Once a diagnosis of IBD has been made, typically by endoscopy, the goals of therapy are to induce and maintain a remission. The least toxic agents which patients are typically treated with are the aminosalicylates. Sulfasalazine (Azulfidine), typically administered four times a day, consists of an active molecule of aminosalicylate (5-ASA) which is linked by an azo bond to a sulfapyridine. Anaerobic bacteria in the colon split the azo bond to release active 5-ASA. However, at least 20% of patients cannot tolerate sulfapyridine because it is associated with significant side-effects such as reversible sperm abnormalities, dyspepsia, or allergic reactions to the sulpha component. These side effects are reduced in patients taking olsalazine. However, neither sulfasalazine nor olsalazine are effective for the treatment of small bowel inflammation. Other formulations of 5-ASA have been developed which are released in the small intestine (e.g. mesalamine and asacol). Normally it takes 6-8 weeks for 5-ASA therapy to show full efficacy. Patients who do not respond to 5-ASA therapy, or who have a more severe disease, are prescribed corticosteroids. However, this is a short term therapy and cannot be used as a maintenance therapy. Clinical remission is achieved with corticosteroids within 2-4 weeks, however the side effects are significant and include a Cushing goldface, facial hair, severe mood swings, and sleeplessness. The response to sulfasalazine and 5-aminosalicylate preparations is poor in Crohn's disease, fair to mild in early ulcerative colitis and poor in severe ulcerative colitis. If these agents fail, powerful immunosuppressive agents such as cyclosporine, prednisone, 6-mercaptopurine or azathioprine (converted in the liver to 6-mercaptopurine) are typically tried. For Crohn's disease patients, the use of corticosteroids and other immunosuppressives must be carefully monitored because of the high risk of intra-abdominal sepsis originating in the fistulas and abscesses common in this disease. Approximately 25% of IBD patients will require surgery (colectomy) during the course of the disease.

Further, the risk of colon cancer is elevated in patients with severe ulcerative colitis, particularly if the disease has existed for several years. About 20-25% of patients with IBD eventually require surgery for removal of the colon because of massive bleeding, chronic debilitating illness, performation of the colon, or risk of cancer. Surgery is also sometimes performed when other forms of medical treatment fail or when the side effects of steroids or other medications threaten the patient's health. As surgery is invasive and drastically life altering, it is not a highly desirable treatment regimen, and is typically the treatment of last resort.

Airway Inflammation

Inflammation of the airway encompasses widespread conditions with complex and multifactorial etiologies. The severity of the conditions vary widely between individuals, and within individuals, dependent on factors such as genetics, environmental conditions, and cumulative respiratory tract pathology associated with duration and severity of disease. Airway inflammation can be the result of immune system hyper-responsiveness to innocuous environmental antigens, with asthma typically including an atopic (i.e., allergic) component.

In asthma, the pathology manifests as inflammation, mucus overproduction, and reversible airway obstruction that may result in scarring and remodeling of the airways. Mild asthma is relatively well controlled with current therapeutic interventions including beta-agonists and low dose inhaled corticosteroids or cromolyn. However, moderate and severe asthma are less well controlled, and require daily treatment with more than one long-term control medication to achieve consistent control of asthma symptoms and normal lung function. With moderate asthma, doses of inhaled corticosteroids are increased relative to those given to mild asthmatics, and/or supplemented with long acting beta-agonists (LABA) (e.g., salmeterol) or leukotriene inhibitors (e.g., montelukast, zafirlukast). Although LABA can decrease dependence on corticosteroids, they are not as effective for total asthma control as corticosteroids (e.g., reduction of episodes, emergency room visits) (Lazarus et al., JAMA. 2001. 285: 2583-2593; Lemanske et al., JAMA. 2001. 285: 2594-2603). With severe asthma, doses of inhaled corticosteroids are increased, and supplemented with both LABA and oral corticosteroids. Severe asthmatics often suffer from chronic symptoms, including nighttime symptoms, limitations on physical activities, and more frequent emergency room visits. Additionally, chronic corticosteroid therapy at any level has a number of unwanted side effects, especially in children (e.g., damage to bones resulting in decreased growth.

Allergic and non-allergic rhinitis and sinusitis is a form of airway inflammation that affects the nasal passages, and is typically associated with watery nasal discharge, sneezing, congestion and itching of the nose and eyes. It is frequently caused by exposure to irritants, particularly allergens. Allergic rhinitis and sinusitis affects about 20% of the American population and ranks as one of the most common illnesses in the US. Most suffer from seasonal symptoms due to exposure to allergens, such as pollen, that are produced during the natural plant growth season(s). A smaller proportion of sufferers have chronic allergies due to allergens that are produced throughout the year such as house dust mites or animal dander. A number of over the counter treatments are available for the treatment of allergic rhinitis and sinusitis, including oral and nasal antihistamines and decongestants. Antihistamines are utilized to block itching and sneezing and many of these drugs are associated with side effects such as sedation and performance impairment at high doses. Decongestants frequently cause insomnia, tremor, tachycardia, and hypertension. Nasal formulations, when taken improperly or terminated rapidly, can cause rebound congestion. Anticholinergics and montelukast have substantially fewer side effects, but they also have limited efficacy. Similarly, prescription medications are not free of side effects. Nasal corticosteroids can be used for prophylaxis or suppression of symptoms; however, compliance is variable due to side effects including poor taste and nasal irritation and bleeding. Allergen immunotherapy is expensive and time consuming and carries a risk of anaphylaxis.

Despite the advances in the treatment for IBD and airway inflammation, there is no cure for either and current therapies have certain limitations and drawbacks. Therefore, there is an unmet need in the medical arts for treating IBD, airway inflammation, cancer and other inflammatory disorders.

BRIEF SUMMARY OF INVENTION

The present invention generally relates to novel compositions and methods for treating diseases or conditions resulting from inflammation (in-whole or in-part) due to an immune response. For example, the present invention is drawn to compositions and methods for the treatment of IBD, airway inflammation, and cancer, as well as other diseases and conditions taught herein.

The inventors have shown that serine protease autotransporters of the Enterobacteriaceae (SPATEs), and in particular, class-2 SPATE proteins, such as Pic, have protease activity against specific proteins involved in cellular immunity, which makes Pic ("protein involved in intestinal colonization"; Henderson et al., Infection and Immunity, November 1999, p. 5587-5596; GenBank Accession No: AAK00464.1) an ideal candidate for perturbing or blunting an immune response in a subject having a disease or condition in which an active immune response is attributable to a cause of the disease or condition.

In certain embodiments, the invention is drawn to methods of decreasing inflammation in a patient, comprising administering to a patient having inflammation, a composition comprising at least one class-2 SPATE protein capable of cleaving proteins involved in an inflammatory immune response. The invention is also drawn to methods of perturbing immune response in a patient comprising administering to a patient having a disease or condition in which an active immune response is attributable to a cause of the disease or condition, a composition comprising at least one class-2 SPATE protein capable of cleaving proteins involved in an inflammatory immune response. According to non-limiting example embodiments, the disease or condition includes at least one of IBD, airway inflammation, cancer or other inflammatory disorders. According to further embodiments, the class-2 SPATE comprises at least one mucin-cleaving class-2 SPATE, such as Pic.

In specific embodiments of the invention, IBD includes, for example, ileitis and colitis caused by Crohn's disease, and ulcerative colitis. Additionally, other intestinal diseases or conditions whereby inflammation contributes to the pathophysiology of the disease or condition can be treated by administering Pic, including, for example, antibiotic-associated intestinal inflammation (including, for example, colitis), ischemic colitis, idiopathic colitis, allergic colitis, and eosinophilic colitis. In other specific embodiments of the invention, airway inflammation includes, for example, chemically or radiologically induced airway inflammation, cystic fibrosis, asthma, chronic bronchitis, Mycoplasma- or Chlamydia-induced airway inflammation, viral bronchitis and bronchiolitis, granulomatous diseases, tracheitis, bronchopulmonary dysplasia, eustachian tube dysfunction, allergic and non-allergic rhinitis and sinusitis, and Acute Respiratory Distress Syndrome (ARDS). Other diseases or conditions whereby inflammation contributes to the pathophysiology of the disease or condition can be treated by administering Pic, including an acute inflammatory disease or condition of the skin or eye (including, for example, impetigo, folliculitis, furuncle, carbuncle, sweat gland abscess, erysipelas, cellulites, episcleritis, scleritis, and uveitis).

Example embodiments are also directed to compositions for treating diseases or conditions resulting from inflammation due to immune response, in which the composition includes at least one class-2 SPATE protein capable of cleaving proteins involved in an inflammatory immune response. The class-2 SPATE protein may include for example, at least one mucin-cleaving class-2 SPATE protein, such as Pic.

The foregoing has outlined rather broadly the features and technical advantages of the present invention in order that the detailed description of the invention that follows may be better understood. Additional features and advantages of the invention will be described herein. It should be appreciated by those skilled in the art that any conception and specific embodiment or aspect disclosed herein may be readily utilized as a basis for modifying or designing other structures for carrying out the same purposes of the present invention. It should also be realized by those skilled in the art that such equivalent constructions do not depart from the spirit and scope of the invention. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

DETAILED DESCRIPTION OF THE INVENTION

I. Definitions

Figure 1:
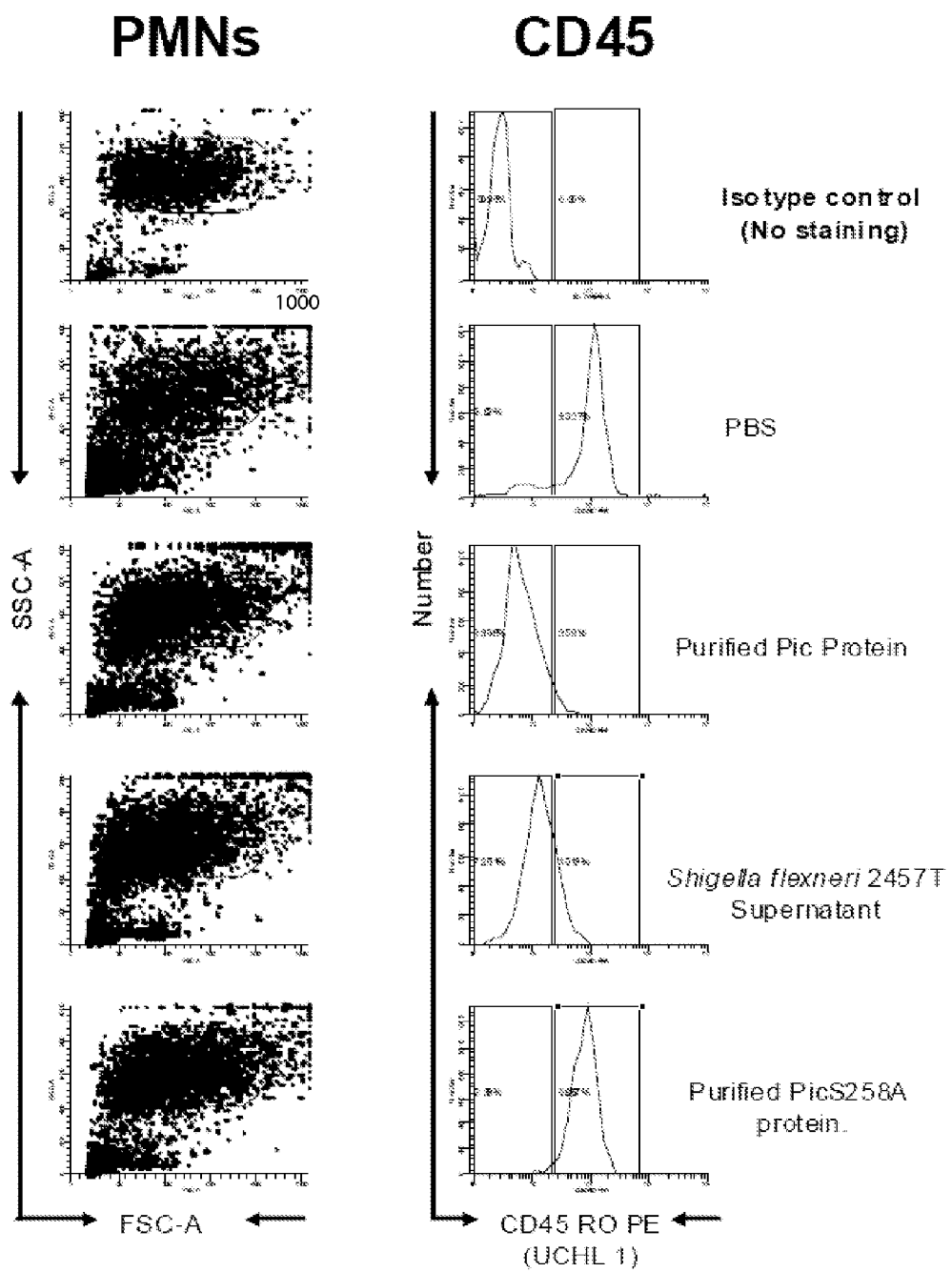
FIG. 1. Degradation of Human Neutrophil CD45 by *S. flexneri* 2457T supernatants and Pic.
Figure 2:
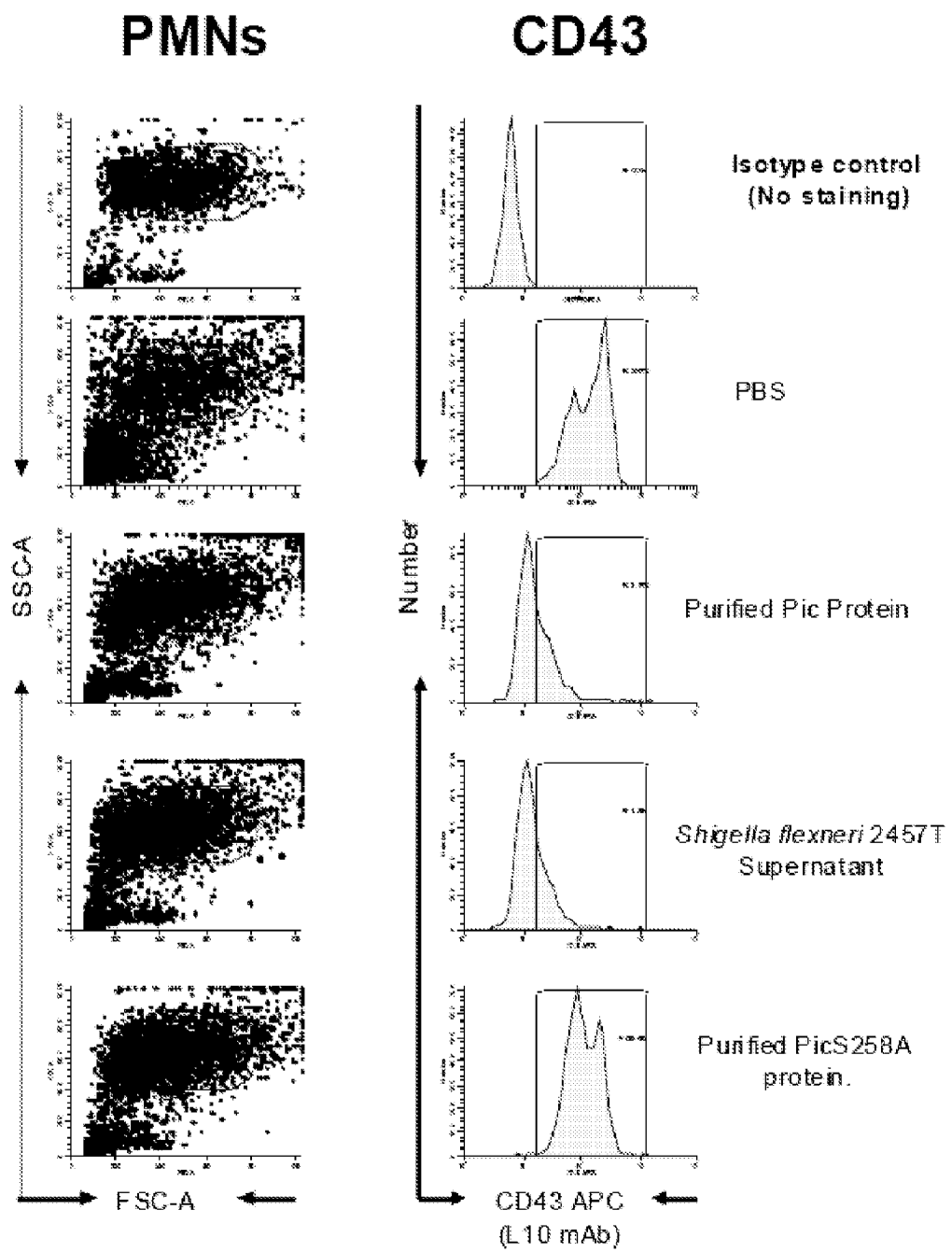
FIG. 2. Degradation of Human Neutrophil CD43 by *S. flexneri* 2457T supernatants and Pic.
Figure 3:
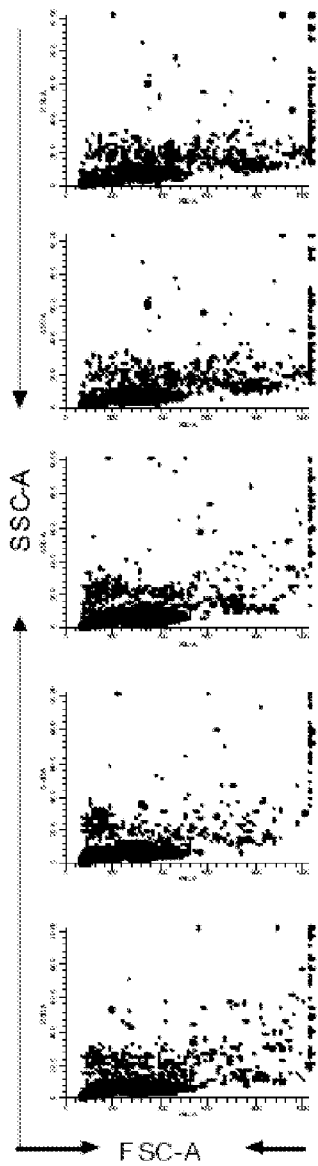
FIG. 3. Pic and *S. flexneri* 2457T supernatants cleave the extracellular domain of Lymphocyte CD43.
Figure 3:
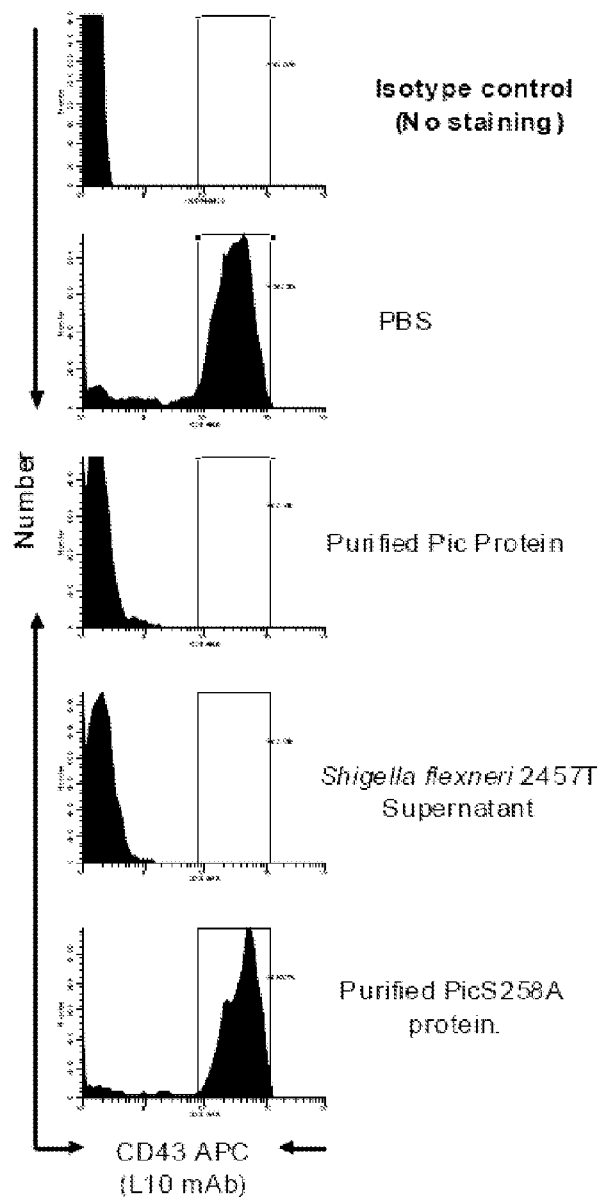
Figure 4:
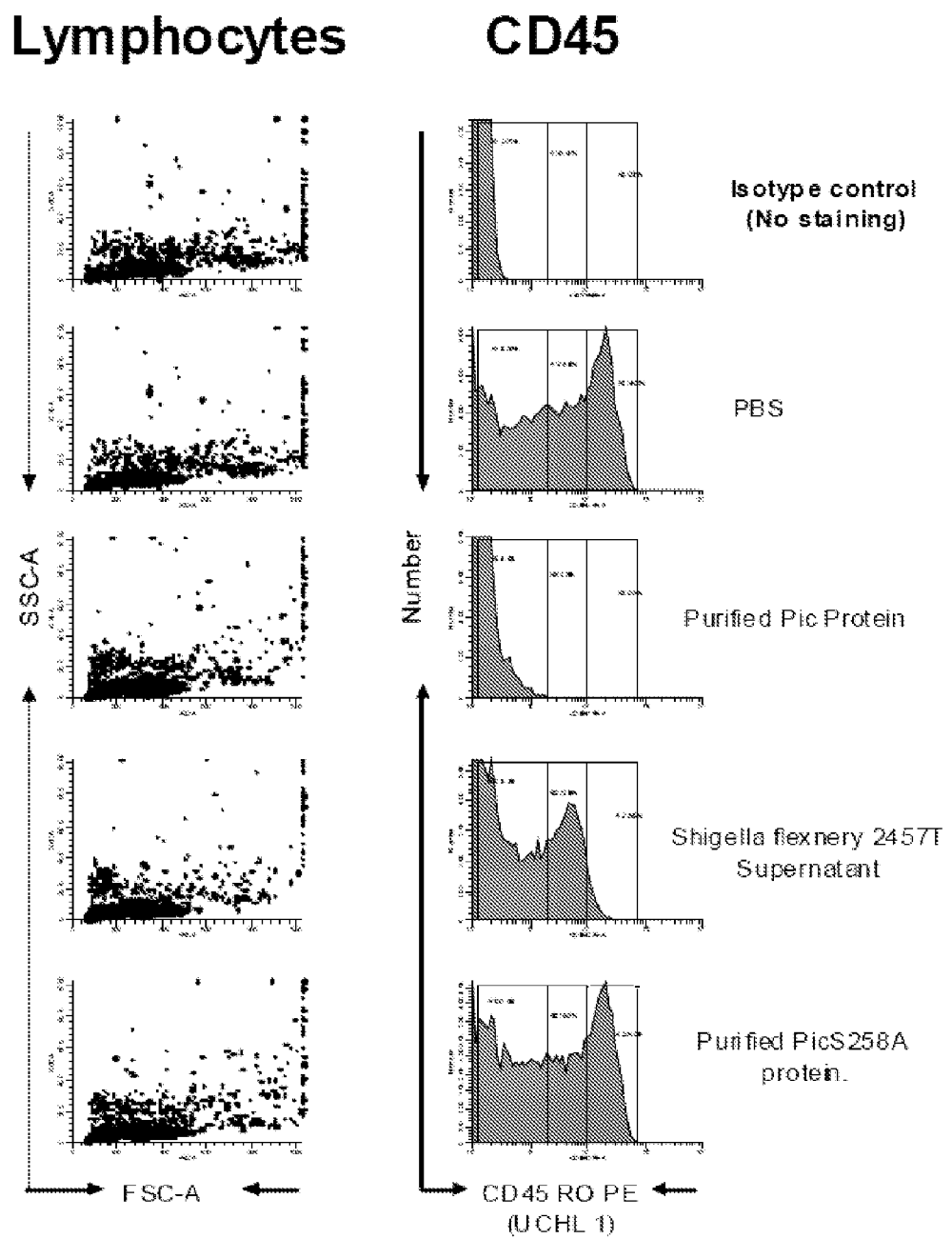
FIG. 4. Pic and *S. flexneri* 2457T supernatants cleave the extracellular domain of Lymphocyte CD45.
Figure 5:
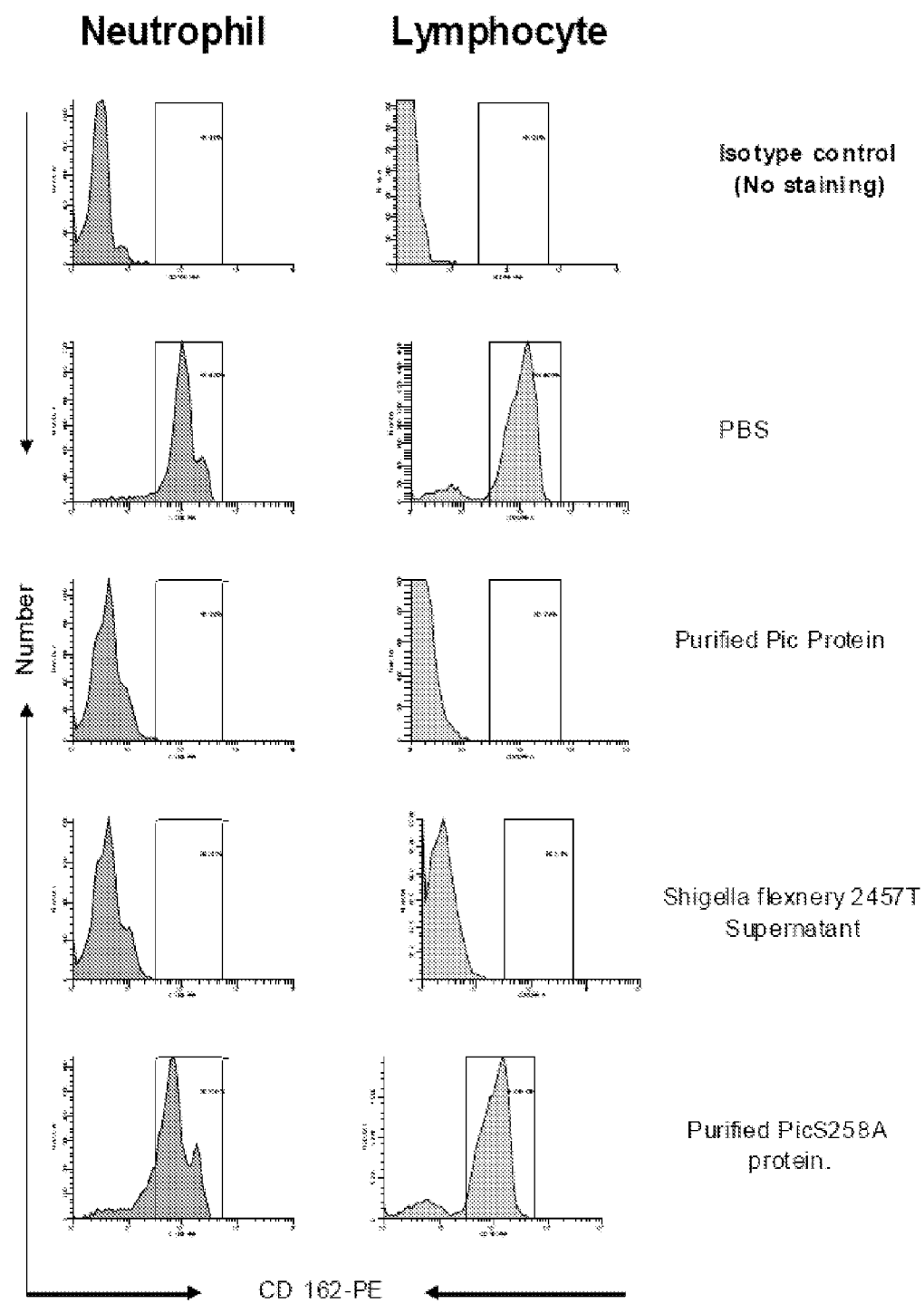
FIG. 5. Pic and *S. flexneri* 2457T supernatants cleave the extracellular domain of neutrophil and Lymphocyte CD 162 (PSGL-1).

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "treat" and all its forms and tenses (including, for example, treating, treated, and treatment) can refer to therapeutic or prophylactic treatment. In certain aspects of the invention, those in need thereof of treatment include those already with a pathological disease or condition of the invention (including, for example, a IBD, airway inflammation, cancer or other inflammatory disorder), in which case treating refers to administering to a subject (including, for example, a human or other mammal in need of treatment) a therapeutically effective amount of a formulation so that the subject has an improvement in a sign or symptom of a pathological condition of the invention, including, for example, a reduction, inhibition, perturbation, or blunting of an immune response (all synonymous with lessening or decreasing inflammation). The improvement may be any observable or measurable improvement. Thus, one of skill in the art realizes that a treatment may improve the patient's condition, but may not be a complete cure of the pathological condition. In other certain aspects of the invention, those in need of treatment include, those in which a pathological disease or condition of the invention (including, for example, IBD, airway inflammation, cancer or other inflammatory disorders) is to be prevented, in which case treating refers to administering to a subject a therapeutically effective amount of a formulation to a subject (including, for example, a human or other mammal in need of treatment) at risk of developing a pathological conditional of the invention.

As used herein, "vector" refers to an entity, which is capable of delivering one or more gene(s) or protein(s) of interest to a cell. In certain aspects of the invention, a vector expresses and secretes a protein of interest (including, for example, Pic). Examples of a vector include, for example, a viral vector, a naked DNA or RNA expression vector, plasmid, cosmid or phage vector, a DNA or RNA expression vector associated with a cationic condensing agent, a DNA or RNA expression vector encapsulated in a liposome, and certain cells (including, for example, a microbial vector).

II. The Present Invention

The present inventors first described a family of serine proteases secreted by all pathogenic E. coli and Shigella spp (Henderson I R, Navarro-Garcia F, & Nataro J P (1998) Trends Microbiol 6, 370-378, Henderson I R & Nataro J P (2001) Infect Immun 69, 1231-1243). This family, called the serine protease autotransporters of Enterobacteriaceae (SPATEs), is translocated across the gram negative outer membrane via the autotransporter pathway, in which a dedicated C-terminal domain of the holoprotein forms a beta-barrel outer membrane species, which, along with accessory proteins, mediates transport of its N-terminus across the outer membrane to the external milieu (Ieva R & Bernstein H D (2009) Proc Natl Acad Sci USA 106, 19120-19125; Ruiz-Perez F, Henderson I R, Leyton D L, Rossiter A E, Zhang Y, & Nataro J P (2009) J Bacteriol 191, 6571-6583; Sauri A, Soprova Z, Wickstrom D, de Gier J W, Van der Schors R C, Smit A B, Jong W S, & Luirink J (2009) Microbiology 155, 3982-3991.) The N-terminus is subsequently cleaved by a protease motif within the beta-barrel, and the processed species is released from the bacterium (Dautin N, Barnard T J, Anderson D E, & Bernstein H D (2007) EMBO J 26, 1942-1952.).

The mature SPATEs are related serine proteases with diverse functions, but the inventors have proposed that these proteases can be divided phylogenetically into two distinct classes, designated 1 and 2 (Dutta P R, Cappello R, Navarro-Garcia F, & Nataro J P (2002) Infect Immun 70, 7105-7113.) Class 1 SPATEs are cytotoxic in vitro and inflict mucosal damage on intestinal explants. Though the mechanisms of class 1 SPATEs are not fully understood, several have been shown to enter eukaryotic cells and to cleave cytoskeletal proteins) Al-Hasani K, Navarro-Garcia F, Huerta J, Sakellaris H, & Adler B (2009) PLoS One 4, e8223; Canizalez-Roman A & Navarro-Garcia F (2003) Mol Microbiol 48, 947-958; Navarro-Garcia F, Canizalez-Roman A, Luna J, Sears C, & Nataro J P (2001) Infect Immun 69, 1053-1060.).

Class 2 SPATEs are more enigmatic. At least four members of the Class 2 SPATEs have been shown to cleave mucins in vitro; these species include the thermostable hemaglutinin (Tsh) from avian pathogenic E. coli, and its nearly identical homolog hemoglobin-binding protein (Hbp) from human extra-intestinal E. coli (Otto B R, van Dooren S J, Nuijens J H, Luirink J, & Oudega B (1998) J Exp Med 188, 1091-1103; Provence D L & Curtiss R, 3rd (1994) Infect Immun 62, 1369-1380); the Pic protease (protease involved in colonization), found in Shigella flexneri, enteroaggregative E. coli (EAEC), and uropathogenic E. coli (UPEC) (Henderson I R, Czeczulin J, Eslava C, Noriega F, & Nataro J P (1999) Infect Immun 67, 5587-5596; Parham N J, Srinivasan U, Desvaux M, Foxman B, Marrs C F, & Henderson I R (2004) FEMS Microbiol Lett 230, 73-83; Rajakumar K, Sasakawa C, & Adler B (1997) Infect Immun 65, 4606-4614.); and the EpeA (EHEC-plasmid encoded autotransporter) from enterohemorrhagic E coli (Leyton D L, Sloan J, Hill R E, Doughty S, & Hartland E L (2003) Infect Immun 71, 6307-6319.).

Pic protein confers a subtle competitive advantage in colonization and acts as a secretagogue in animal models (Harrington S M, Sheikh J, Henderson I R, Ruiz-Perez F, Cohen P S, & Nataro J P (2009) Infect Immun 77, 2465-2473; Navarro-Garcia F, Gutierrez-Jimenez J, Garcia-Tovar C, Castro L A, Salazar-Gonzalez H, & Cordova V Infect Immun 78, 4101-4109). The inventors have recently reported that cleavage of mucin by Pic may release substrates that can be metabolized by the colonizing host bacterium. However, the fact that not all producers of the Class 2 mucinases are mucosal pathogens suggested that cleavage of mucin substrates may provide some additional fundamental advantage to the pathogen prompting the studies described here.

A variety of leukocyte surface glycoproteins with vital roles in numerous cellular functions are substituted with carbohydrates structurally similar to those found on human mucins. These glycoproteins play roles in diverse functions including cell growth, differentiation, embryogenesis, immune cell response, cancer metastasis and signal transduction events (Ohtsubo K & Marth J D (2006) Cell 126, 855-867; Marth J D & Grewal P K (2008) Nat Rev Immunol 8, 874-887.)

The inventors show herein that the substrates of the mucin-cleaving class 2 SPATEs include mucin-like glycoproteins on the surface of nearly all lineages of hematopoietic cells. Such targets, including CD43, CD44, CD45, CD93, fractalkine and PSGL-1, may have broad effects on the immune response, including leukocyte apoptosis, activation, migration and signaling. The inventors' data suggest broadly important mechanisms for these common virulence factors.

Pic ("protein involved in intestinal colonization") is a 109 kDa serine protease that is encoded by strains of enteroaggregative *Escherichia coli*, uropathogenic *E. coli*, and *Shigella flexneri* (Henderson et al., Infection and Immunity, November 1999, p. 5587-5596; GenBank Accession No: AAK00464.1). It has been found occasionally among non-pathogenic *E. coli* strains, including the commensal strain called Nissle.

It has previously been reported that the Pic is a mucinase that promotes colonization of the mouse gastrointestinal tract in an *E. coli* background (Harrington et al., Infect Immun. 2009 June; 77(6):2465-73). The present inventors have shown that Pic is able to cleave proteins that are mounted on the surface of human leukocytes. The inventors have tested purified Pic against purified polymorphonuclear cells and human lymphocytes. The protein can be prepared from the supernatant of an *E. coli* strain, either a pathogenic strain or a laboratory strain in recombinant form. The Pic-encoding gene is already available in a cloned form on the plasmid pPic.

The proteins that are cleaved from the surface of polymorphonuclear cells and lymphocytes are proteins that are involved in cell migration, adherence, and signaling. Therefore, in certain aspect of the invention the activity of Pic will result in inhibition of the activity of these and other leukocytes in a mammalian host (including, for example, a human, non-human primate, dog, cat, pig, sheep, mouse, rat, horse, and other domestic, farm, exotic, and wild animals). In specific aspects, the inhibition of the activity of these and other leukocytes occurs at the mucosal surface in the gastrointestinal tract or respiratory tract.

The inventors have shown that class-2 SPATE proteins and in particular, mucin-cleaving class-2 SPATEs and even more particular, Pic, has protease activity against specific proteins involved in cellular immunity, which makes Pic an ideal candidate for perturbing or blunting an immune response in a subject having a disease or condition in which an active immune response is attributable to a cause of the disease or condition. In particular aspects of the invention, Pic is able to perturb or blunt an immune response at mucosal surfaces. Considering that the extent and severity of injury, including mucosal injury, in IBD and airway inflammation is determined by the disequilibrium between inflammation versus reparative and cytoprotective mechanisms, the newly discovered properties of Pic to cleave proteins involved in an inflammatory immune response makes Pic an ideal candidate for treating IBD, airway inflammation, and inflammatory disorders.

Thus, non-limiting examples of the present invention include compositions for treating diseases or conditions resulting from inflammation due to an immune response, which include at least one class-2 SPATE protein capable of cleaving proteins involved in an inflammatory immune response. According to non-limiting embodiments, the class-2 SPATE protein may be present in an amount effective for decreasing inflammation in a patient having inflammation. According to other non-limiting embodiments, the class-2 SPATE protein may be present in an amount effective for perturbing immune response in a patient having a disease or condition in which an active immune response is attributable to a cause of the disease or condition According to non-limiting example embodiments, the at least one class-2 SPATE protein comprises at least one mucin-cleaving class-2 SPATE protein. Example mucin-cleaving class-2 SPATE proteins may include those selected from the group consisting of thermostable hemaglutinin (Tsh); hemoglobin-binding protein (Hbp); Pic protease (protein involved in intestinal colonization); and EpeA (EHEC-plasmid encoded autotransporter). According to further embodiments the at least one class-2 SPATE protein comprises protein involved in intestinal colonization (Pic).

In certain aspects of the invention, an inflammatory immune response includes, for example, cytokine release, neutrophil acitivation and chemotaxis, and transendothelial migration.

In other aspects of the invention, a disease or condition in which Pic is able to perturb or blunt an immune response includes, for example, IBD, airway inflammation, cancer and other inflammatory disorders. IBD includes, for example, ileitis and colitis caused by Crohn's disease and ulcerative colitis. Additionally, other intestinal diseases or conditions whereby inflammation contributes to the pathophysiology of the disease or condition can be treated by administering Pic, and include, for example, antibiotic-associated intestinal inflammation (including, for example, colitis), ischemic colitis, idiopathic colitis, allergic colitis, and eosinophilic colitis. Airway inflammation includes, for example, chemically or radiologically induced airway inflammation, cystic fibrosis, asthma, chronic bronchitis, Mycoplasma, Chlamydia, and viral bronchitis and bronchiolitis, granulomatous diseases, tracheitis, bronchopulmonary dysplasia, eustachian tube dysfunction, allergic rhinitis and sinusitis, and Acute Respiratory Distress Syndrome (ARDS). Other diseases or conditions whereby inflammation contributes to the pathophysiology of the disease or condition can be treated by administering Pic, including an acute inflammatory disease or condition of the skin or eye (including, for example, impetigo, folliculitis, furuncle, carbuncle, sweat gland abscess, erysipelas, cellulites, episcleritis, scleritis, and uveitis).

Example embodiments of the present invention include methods of perturbing immune response in a patient comprising administering to a patient having a disease or condition in which an active immune response is attributable to a cause of the disease or condition, a composition comprising at least one class-2 SPATE protein capable of cleaving proteins involved in an inflammatory immune response.

According to example embodiments, in these methods the at least one class-2 SPATE protein comprises at least one mucin-cleaving class-2 SPATE protein. Non-limiting examples may be selected from the group consisting of thermostable hemaglutinin (Tsh); hemoglobin-binding protein (Hbp); the Pic protease (protein involved in intestinal colonization); and EpeA (EHEC-plasmid encoded autotransporter). According to further embodiments, the at least one class-2 SPATE comprises protein involved in intestinal colonization (Pic). According to further examples, the disease or condition includes at least one of IBD, airway inflammation, and cancer, and other inflammatory disorders. Other examples may include cancer or other inflammatory disorders. Class-2 SPATE protein may be present in an amount effective for perturbing immune response in a patient having a disease or condition in which an active immune response is attributable to a cause of the disease or condition.

Example embodiments also include methods of decreasing inflammation in a patient, which include administering to a patient having inflammation a composition comprising at least one class-2 SPATE protein capable of cleaving proteins involved in an inflammatory immune response. According to non-limiting example embodiments, the at least one class-2 SPATE protein includes at least one mucin-cleaving class 2 SPATE protein, including, but not limited to thermostable hemaglutinin (Tsh); hemoglobin-binding protein (Hbp); the Pic protease (protease involved in colonization); and EpeA (EHEC-plasmid encoded autotransporter).

According to example embodiments, in these methods the at least one class-2 SPATE comprises protein involved in intestinal colonization (Pic). According to non-limiting embodiments, the Class-2 SPATE protein may be present in an amount effective for decreasing inflammation in a patient having inflammation.

In other aspects of the invention, the compositions and/or effective ingredient, such as Pic, is delivered to a site of action by direct administration of the effective ingredient (e.g., Pic) to the site of action in a patient. By way of example, the composition that includes the Pic protein can be aerosolized into an aerosolized composition, or formulated as a topical composition for topical administration to a patient. For example, in the case of treating an airway inflammation, Pic can be delivered by aerosol inhalation. In addition, direct administration of Pic to the site of action can be employed to treat an acute inflammatory disease or condition of the skin or eye. Thus, according to non-limiting example embodiments, in the present methods, administering may include direct administration of the class-2 SPATE to the site of action. According to further embodiments, the formulation may be aerosolized or formulated as a topical composition for topical administration.

In the present methods, the compositions may be administered to the patient by at least one method selected from the group consisting of topical, inhalation, intranasal, oral and intravenous administration, or other administration methods, which may be known to those skilled in the art.

Those skilled in the art will understand that the present compositions or formulations may further include one or more pharmaceutically acceptable excipients, which may be desired and/or required depending on the intended form of administration.

In other aspects of the invention, Pic is delivered to its site of action by a microbial vector comprising a gene encoding a class-2 SPATE protein.

Thus, the present invention is directed to a bacterial vector comprising a gene encoding the Pic protein. The microbial vector can be given orally. Oral vaccines have been given for some time now, and a similar strategy may be used to deliver Pic to the site of action. Examples of bacterial vectors include, for example, non-pathogenic *E. coli* engineered to express and secrete Pic. Such bacterial vectors include, for example, the *E. coli* K12 strain called C600 and the commensal *E. coli* strains designated Nissle and HS. Thus, example embodiments are directed to microbial vectors comprising a class-2 SPATE gene. According to non-limiting embodiments, the class-2 SPATE gene comprises the Pic gene.

In particular aspects of the invention drawn to a microbial vector comprising a gene encoding the Pic protein. Pic is expressed by heterologous expression or modification of expression of the existing gene and can be used as a probiotic. For example, a microbial vector is a vector that includes non-pathogenic members of the genus *Aspergillus, Bacillus, Bacteroides, Bifidobacterium, Lactobacillus, Leuconostoc, Pediococcus, Propionibacterium, Saccharomyces, Enterococcus* (including, for example, the *E. coli* K12 strain called C600 and the commensal *E. coli* strains designated Nissle and HS), and probiotics known to those of ordinary skill in the art that express and secrete Pic (or genetically engineered to do the same). In certain aspects of the invention drawn to heterologous expression of Pic, heterologous expression is a result of genetic engineering of a cell or cells whereby DNA is engineered into a cell or cells that do not normally contain the DNA, so that the cell or cells produce a protein corresponding to the DNA. Methods for accomplishing heterologous expression is known to those of ordinary skill in the art (see, for example, Sambrook et al., Molecular Cloning: A Laboratory Manual, 2nd ed., Cold Spring Harbor Laboratory, Cold Spring Harbor, N.Y. (1989); Sambrook et al., Molecular Cloning: A Laboratory Manual, 3rd ed., Cold Spring Harbor Laboratory Press, Cold Spring Harbor, N.Y. (2001); Watson et al., Recombinant DNA, 2nd ed., Scientific American Books, New York, N.Y. (1992); Watson et al., Recombinant DNA: Genes and Genomes—A Short Course, 3rd ed., Scientific American Books, New York, N.Y. (2007)). In certain aspects of the invention drawn to modification of expression of an existing gene, modification refers to increasing or decreasing the expression of the gene for Pic. In particular aspects of the invention, modification of expression refers to increasing the expression of the gene for Pic. For example, a bacterium or other microbe that contains the Pic gene can be engineered to increase its expression of this gene. Methods for accomplishing modification of expression are known to those of ordinary skill in the art (see, for example, Sambrook et al., Molecular Cloning: A Laboratory Manual, 2nd ed., Cold Spring Harbor Laboratory, Cold Spring Harbor, N.Y. (1989); Sambrook et al., Molecular Cloning: A Laboratory Manual, 3rd ed., Cold Spring Harbor Laboratory Press, Cold Spring Harbor, N.Y. (2001); Watson et al., Recombinant DNA, 2nd ed., Scientific American Books, New York, N.Y. (1992); Watson et al., Recombinant DNA: Genes and Genomes—A Short Course, 3rd ed., Scientific American Books, New York, N.Y. (2007)). Any step of gene expression may be modulated or otherwise altered to accomplish modification of expression, including for example, modulation or otherwise altering a step at the level of transcriptional regulation, post-transcriptional regulation, translational regulation, and post-transcriptional regulation. The stability of the final gene product, whether it is RNA or protein, also contributes to the expression level of the gene; an unstable product results in a low expression level. In general, gene expression is regulated through changes in gene copy number and the number and type of interactions between molecules that collectively influence transcription of DNA, stability or degradation of DNA, translation of RNA, stability or degradation of RNA, and stability or degradation of protein. For example, modification of expression at the level of transcriptional regulation, post-transcriptional regulation, translational regulation, and post-transcriptional regulation, includes for example, an increase in gene copy, an increase in gene or protein stability, gene amplification, a modification or addition of a promoter (e.g., a constitutively active promoter), and a modification or addition of an initiator or binding site.

In particular aspects of the invention drawn to administration of Pic for treating antibiotic-associated intestinal inflammation, the antibiotic can be any antibiotic that causes intestinal inflammation. For example, an antibiotic that causes intestinal inflammation may include, antibiotic-associated intestinal inflammation a 2,4-diaminopyrimidine, an aminoglycoside, an amphenicol, an ansamycin, a beta-lactam, a carbapenem, a cephalosporin, a fluoroquinolone, a glycylcycline, a lincosamide, a macrolides, a monobactam, a nitrofuran, and oxazolidinone, a penicillin, a polypeptide, a quinolones or quinoline analog, a sulfonamide, a sulfone, a tetracycline, or other miscellaneous class of antibacterial compound. In specific aspects, the one or more other antibacterial compound can be, for example, amdinocillin (mecillinam), amikacin, amoxicillin, amoxicillin+clavulanate, ampicillin, ampicillin+sulbactam, atovaquone, azithromycin, aztreonam, bacampicillin, bacitracin, capreomycin, carbenicillin indanyl sodium, cefaclor, cefadroxil, cefamandole, cefazolin, cefdinir, cefditoren, cefepime, cefixime, cefmetazole, cefonicid, cefoperazone, cefotaxime, cefotetan, cefoxitin, cefpodoxime, proxetil, cefprozil, ceftazidime, ceftibuten, ceftizoxime, ceftriaxone, cefuroxime and cefuroxime axetil, cephalexin, cephalothin, cephapirin, cephradine, chloramphenicol, cinoxacin, ciprofloxacin, clarithromycin, clindamycin, cloxacillin, colistimethate, cycloserine, daptomycin, demeclocycline, dicloxacillin, dirithromycin, doripenem, doxycycline, enoxacin, ertapenem, erythromycin, fosfomycin, gatifloxacin, gemifloxacin, gentamicin, grepafloxacin, imipenem/cilastatin, imiquimod, kanamycin, levofloxacin, lincomycin, linezolid, lomefloxacin, loracarbef, mafenide, malathion, meropenem, methenamine hippurate, methicillin, metronidazole, mezlocillin, minocycline, moxifloxacin, mupirocin, nafcillin, nalidixic acid, neomycin, netilmicin, nitrofurantoin, nitrofurazone, norfloxacin, novobiocin, ofloxacin, oxacillin, oxytetracycline, penicillin, piperacillin, piperacillin+tazobactam, podofilox, polymyxin B, quinupristin+dalfopristin, retapamulin, rifapentine, rifaximin, saturated solution of potassium iodide, sparfloxacin, spectinomycin, streptomycin, sulfadiazine, sulfamethoxazole, sulfisoxazole, sulphur precipitated in petrolatum, trichloroacetic acid, bichloroacetic acid, teicoplanin, telithromycin, terbinafine, tetracycline, ticarcillin, ticarcillin+clavulanic acid, tigecycline, tobramycin, trimethoprim, trimethoprim+sulfamethoxazole, trovafloxacin, and vancomycin.

In other aspects of the invention, Pic is administered in combination with at least one other treatment known to one of ordinary skill in the art for treating a disease or condition described herein. Non-limiting example embodiments include methods that include administering to the patient at least one additional treatment or composition for treating a disease or condition caused by inflammation. In such instances, the composition that includes Pic or other class-2 SPATE protein can be administered prior to, concurrent with, or after the on-set or duration of the other treatment known to one of ordinary skill in the art for treating a disease or condition described herein. Thus, the at least one additional composition may be administered to the patient prior to, concurrently with, or after administration of the composition comprising at least one class-2 SPATE protein. For the purposes of illustration, treatments for IBD are discussed further and used as an example. Therefore, for the purposes of illustration Pic can be administered prior to, concurrent with, or preceding the on-set or duration a treatment for IBD. As discussed further below, non-limiting example embodiments of the at least one additional treatment or composition that may be administered include aminosalicylates, corticosteroids, immunomodulators, antibiotics, probiotics and biologics.

Medical treatment for IBD (including, for example, Crohn's disease and ulcerative colitis) has two main goals: achieving remission (the absence of symptoms) and, once that is accomplished, maintaining remission (prevention of flare-ups). To accomplish these goals, treatment is aimed at controlling the ongoing inflammation in the intestine, which is the cause of IBD symptoms. There is no standard regimen for managing all patients with IBD. The symptoms, course of disease, and prognosis vary considerably. Proper disease treatment depends upon an accurate diagnosis. This typically requires endoscopic (the use of lighted tubes to view the intestine), radiologic (X-rays), and pathologic (analysis of tissues) examinations. Current therapies available to IBD patients include, for example, administering aminosalicylates, corticosteroids, immunomodulators, antibiotics, probiotics, and biologics.

A current treatment for IBD is aminosalicylates. Aminosalicylates are compounds that contain 5-aminosalicylic acid (5-ASA). These drugs, which can be given either orally or rectally, interfere with the body's ability to control inflammation. They are effective in treating mild-to-moderate episodes of ulcerative colitis and Crohn's disease, as well as preventing relapses and maintaining remission. Sulfasalazine (AZULFIDINE), the first aminosalicylate to be widely used for IBD, is effective for achieving and maintaining remission in people with mild-to-moderate disease. The active portion of the drug, 5-ASA, is bonded to sulfapyridine, a compound that delivers 5-ASA to the intestine. Other non-sulfapyridine drugs include, for example, mesalamine (ASACOL, PENTASA, APRISO, LIALDA); olsalazine (DIPENTUM); and balsalazide (COLAZAL).

Another current treatment for IBD is corticosteroids. Corticosteroids were first introduced as therapy for IBD in the 1950s. Since that time, these powerful and fast-acting anti-inflammatory drugs have been the mainstay of treatment for acute flare-ups of the disease. Most patients notice an improvement in symptoms within days of starting corticosteroids. In addition to their anti-inflammatory action, corticosteroids also are immunosuppressive. That means they decrease the activity of the immune system, which experts believe may be overactive in people with IBD. As a result, corticosteroids may make certain individuals more susceptible to infection. Corticosteroids closely resemble cortisol, a hormone naturally produced by the body's adrenal glands. This group of medications is available in oral, rectal, and intravenous forms. When patients take corticosteroids, their adrenal glands stop producing or slow down the production of normal cortisol. In general, corticosteroids are recommended only for short-term use in order to achieve remission. As valuable as they are in acute situations, corticosteroids are not effective in preventing flare-ups and therefore are rarely used for maintenance therapy in IBD. In addition, long-term use is not advised because of undesirable side effects, including increased susceptibility to infection. For this reason, corticosteroids are usually given in the lowest possible dosage for the shortest amount of time. Frequent short-duration use, however, is not recommended.

Non-limiting example embodiments also relate to "Use" of a class-2 SPATE protein including, but not limited to mucin-cleaving class-2 SPATE proteins. to reduce inflammation in a patient having inflammation due to an immune response.

Another current treatment for IBD is immunomodulators. As the name implies, immunomodulators weaken or modulate the activity of the immune system. That, in turn, decreases the inflammatory response. Immunomodulators are most often used in organ transplantation to prevent organ rejection, and in autoimmune diseases such as rheumatoid arthritis. Since the late 1960s, immunomodulators have also been used to treat patients with IBD. Two of the first immunomodulators to be used widely in IBD are azathioprine (IMURAN, AZASAN) and 6-mercaptopurine (6-MP, PURINETHOL), drugs that are chemically quite similar. These and other immunomodulators are used to maintain remission in Crohn's disease and ulcerative colitis. Both azathioprine and 6-mercaptopurine have a slow onset of action (generally, three to six months for full effect). Accordingly, they are usually given along with another faster-acting drug (such as corticosteroids). Other immunomodulators to treat IBD are cyclosporine A (SANDIMMUNE, NEORAL) and tacrolimus (PROGRAF), both used for organ transplantation as well. Cyclosporine A has a more rapid onset of action (one to two weeks) than azathioprine and 6-MP. It is useful in people with active Crohn's disease, but only when given intravenously and at high doses. Both cyclosporine A and tacrolimus have been more effective in treating people with severe ulcerative colitis, and are generally given until one of the sloweracting immunomodulators begin to work or until the patient undergoes curative surgery. Tacrolimus can be used in Crohn's disease when corticosteroids are not effective or when fistulas develop.

Another current treatment for IBD is antibiotics. Antibiotics are frequently used as a primary treatment approach in IBD, even though no specific infectious agent has been identified as the cause of these illnesses. However, researchers believe that antibiotics can help control symptoms of IBD by reducing intestinal bacteria and by directly suppressing the intestine's immune system. Antibiotics are effective as longterm therapy in a minority of patients with IBD, particularly Crohn's disease patients who have fistulas (abnormal channels between two loops of intestine, or between the intestine and another structure—such as the skin), or recurrent abscesses near the anus. Patients whose active disease is successfully treated with antibiotics may be kept on these as maintenance therapy as long as the medications remain effective. Although there are several antibiotics that may be effective for certain people, the two most commonly prescribed for treating IBD are metronidazole (FLAGYL) and ciprofloxacin (CIPRO).

Another current treatment for IBD is probiotics. Probiotics are defined as mono- or mixed cultures of live micro-organisms which, when given to a human or other mammal, beneficially affect the host by improving the properties of the indigenous intestinal microflora. Both *Lactobacilli* spp. and *Bifidobacterium* spp. are frequently used as probiotics. Probiotic bacteria for humans are preferably of human origin; they have to be safe for the host, genetically stable, and capable of surviving passage through the gastrointestinal tract (Holzapfel et al., Int J Food Microbiol 1998; 41: 85-101). Among the effects claimed for probiotics are beneficial immunomodulation, reduction of serum cholesterol, improved lactose digestion, and protection against colon cancer (Holzapfel et al., Int J Food Microbiol 1998; 41: 85-101; Gorbach S L. Ann Med 1990; 22: 37-41). Probiotics have also been studied in infectious diarrhoea, IBD, and pouchitis (Gorbach S L. Ann Med 1990; 22: 37-41; Campieri et al., Gastroenterology 1999; 116: 1246-9). Probiotics that have been shown to be effective for treating IBD, include, for example, non-pathogenic *E. coli* (including, for example, *E. coli* Nissle 1917), *Saccharomyces boulardii*, *Bifidobacterium* species, *Lactobacillus* species (including, for example, *Lactobacillus GG*, *Lactobacillus salivarius*, and *Lactobacillus plantarum*), *Clostridium butiricum*, and multispecies probiotics (including, for example, VSL#3 (three strains of bifidobacteria, four of *lactobacilli*, and one of *Streptococcus salivarius* sp. Thermophilus)). Though probiotics may provide some benefit in current form their contribution is relatively minor, and unable to replace the more intensive therapeutics. Means of augmenting the effects of probiotics, such as via the expression of the Pic gene, may provide a dramatic advance in therapy and control of IBD.

The newest class of drugs used for treating IBD is biologics. This class of drugs includes adalimumab (HUMIRA), certolizumab pegol (CIMZIA), infliximab (REMICADE), and natalizumab (TYSABRI). Biologics are genetically engineered medications made from living organisms and their products, such as proteins, genes, and antibodies. Biologics can be used to interfere with the body's inflammatory response in IBD by targeting specific molecular players in the inflammatory process such as cytokines. Promising targets include tumor necrosis factor (TNF)-alpha, interleukins, adhesion molecules, colony-stimulating factors, and others. Learning how these factors work has enabled researchers to design targeted treatment approaches that interrupt inflammation at various stages. Biologics can offer a distinct advantage in IBD treatment. Their mechanism of action is targeted. Unlike corticosteroids, which tend to suppress the entire immune system and thereby produce major side effects, biologics can act selectively. Therapies are targeted to particular enzymes and proteins that have already been proven defective, deficient, or excessive in people with IBD and in animal models of IBD.

Despite advances in medical therapies, some people with IBD eventually will require surgery, either to control their disease or to address various complications. Surgical intervention is integral to the care of people with IBD, and surgical consultants experienced in IBD are vital to proper treatment. Knowing when surgery is indicated and how to operate on these diseases is of paramount importance to both immediate and long-term outcomes.

In view of the above, non-limiting example embodiments of the present invention include methods that include administering at least one additional treatment for a disease or condition caused by inflammation, wherein the at least one additional treatment comprises one or more treatments selected from the group consisting of administering aminosalicylates, corticosteroids, immunomodulators, antibiotics, probiotics, and biologics to the patient in addition to the formulation comprising at least one class-2 SPATE. Such additional compositions may be administered prior to, concurrently with, or after administration of the therapeutically effective amount of a formulation comprising at least one class-2 SPATE.

Also provided herein is the use of class 2 SPATES, and pic in particular for reducing inflammation in a patient.

While the invention has been described with reference to certain particular embodiments thereof, those skilled in the art will appreciate that various modifications may be made without departing from the spirit and scope of the invention.

III. Examples

Example 1

Pic Involvement in an Inflammatory Immune Response

Figure 6:
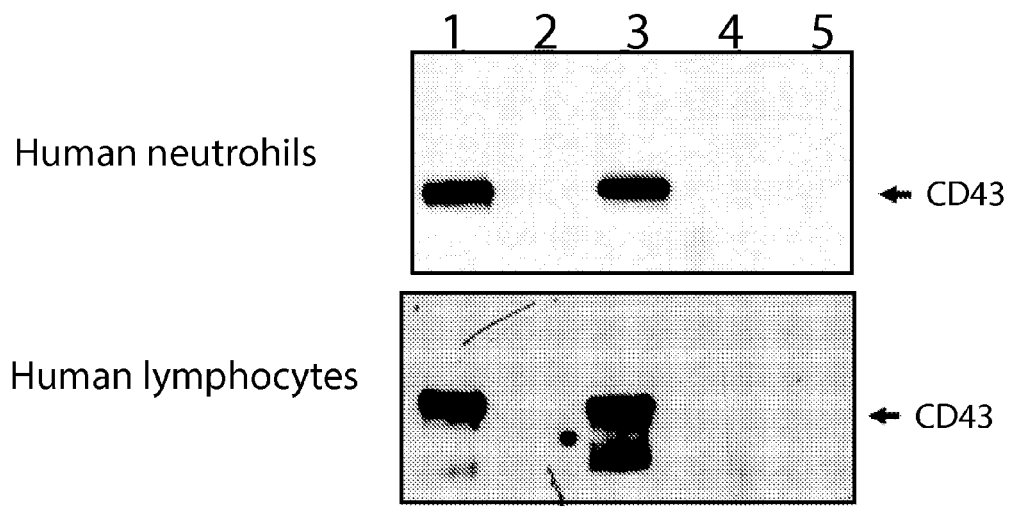
FIG. 6. Degradation of CD43 on Human Leukocytes by Pic. 1. PBS; 2. *S. flexneri* 2457T wt, supernatants; 3. *S. flexneri* 2457T delta-Pic supernatants; 4. *S. flexneri* 2457T delta-sigA supernatants; 5. purified Pic.
Figure 7:
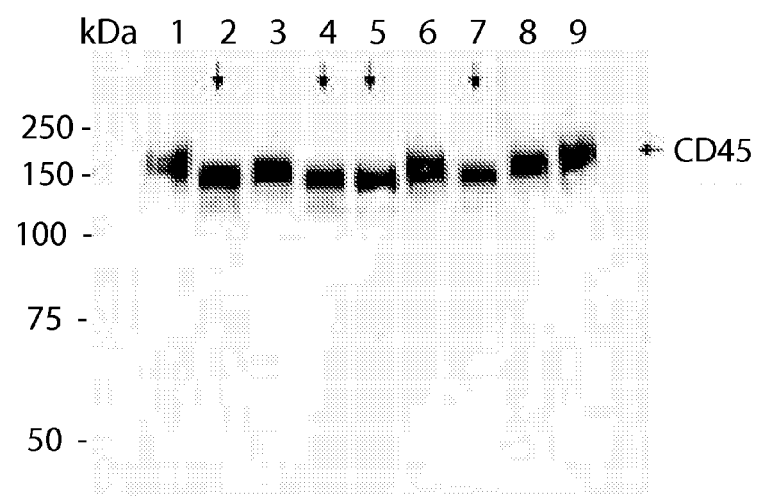
FIG. 7. Degradation of CD45 on lmyphocytes by Pic from *S. flexneri* 2457T. 1—PBS; 2—*S. flexneri* 2457T wt supernatant; 3—*S. flexneri* 2457T delta-pic supernatant; 4—*S. flexneri* 2457T delta-sigA supernatant; 5—purified Pic protein; 6—purified sigA; 7—*S. flexneri* 2457T wt supernatant; 8—*S. flexneri* 2457T delta-Pic supernatant; and 9—PBS.
Figure 8:
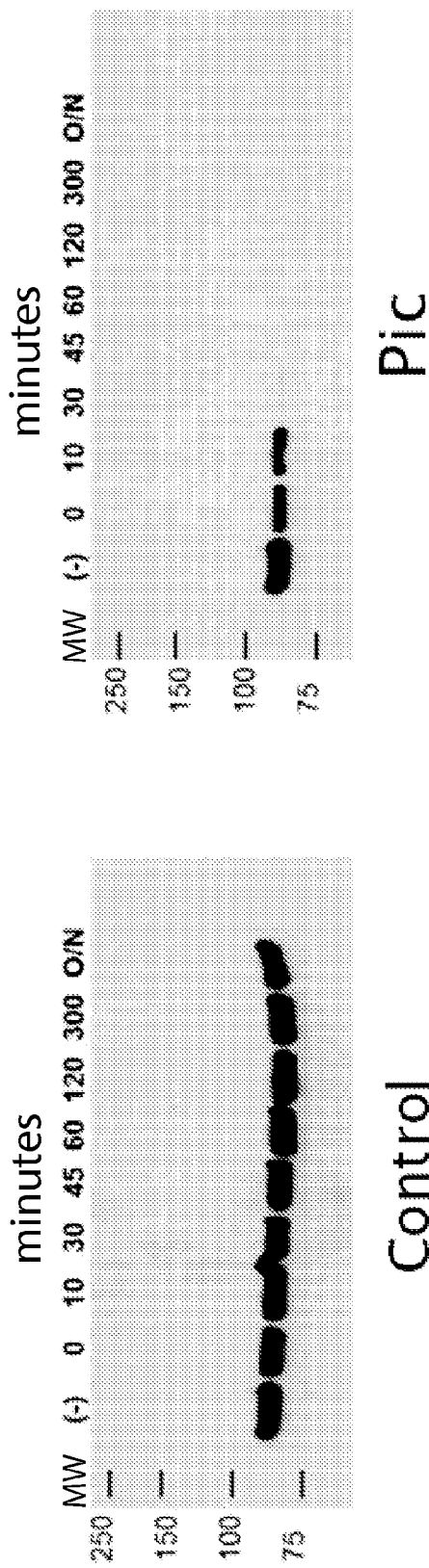
FIG. 8. Pic Cleavage of C1 esterase inhibitor.

The inventors have tested the activity of Pic in three forms: 1) purified from the supernatant of *E. coli* K12 expressing pPic; 2) from the crude supernatant of *Shigella flexneri* strain 2457T; and 3) in mutant form S258A, in which the catalytic serine is changed to the inactive alanine residue. Using these three forms, the inventors demonstrated that Pic cleaves particular proteins involved in a cellular inflammatory immune response, including, for example, CD43 (FIGS. 2, 3, and 6), CD45 (FIGS. 1 and 4), CD 162 (FIG. 5) on both lymphocytes and polymorphonuclear cells, whereas the S258A mutant is unable to cleave any of these proteins. The inventors demonstrate cleavage by treating purified lymphocytes and polymorphonuclear cells (PMNs), then lysing the cells and separating them by SDS-PAGE, followed by immunoblot with anti-CD43 or CD45 antibodies. These experiments demonstrated loss of CD43 on both cells types in the presence of the active protease; CD45 was not completely lost, but was rather degraded to a lower molecular weight form (FIG. 7). Perturbation of these molecules was also demonstrated using fluorescence activated cell sorting (FACS), in which the signal generated by anti-CD43 or anti-CD45 antibodies onto purified lymphocytes or PMNs was abolished by pre-treatment of the cells for 30 minutes with either purified Pic or *S. flexneri* supernatants (FIGS. 1-5). There was no loss of signal when the cells were treated with the mutant form of Pic. By immunoblot, Pic was also found to cleave the complement inhibitor protein C1 esterase inhibitor (FIG. 8). C1 esterase inhibitor (C1-INH) is a protein found in the fluid part of the blood that controls C1, the first component of the complement system. The complement system is a group of proteins that move freely through the bloodstream. These proteins work with the immune system and play a role in the development of inflammation. There are at least nine major complement proteins, designated C1 through C9.

Example 2

Inflammatory Bowel Disease

Various models of IBD are used to determine whether or not a particular intervention is efficacious. IBD animal models can be divided into 5 different categories: (1) antigen-induced colitis and colitis induced by microbials; (2) other inducible forms of colitis (e.g., chemical, immunological, and physical); (3) genetic colitis models (e.g., transgenic and knock-out models); (4) adoptive transfer models, and (5) spontaneous colitis models. Such models and experimental designs are known in the art including, for example, DSS-induced colitis model, IL-10 knockout mouse, A20 knockout mouse, TNBS-induced colitis model, IL-2 knockout mouse, TCR-alpha receptor knockout mouse, and the E-cadherin knockout mouse (see, for example, US Patent Application Publication Nos. 20090312259; 20090312243; 20090311261; 20090311228; 20090306045; 20090274662; 20090263855; 20090263482; 20090214630; 20090209565; and 20070128303; and U.S. Pat. Nos. 7,625,876; 7,560,436; 7,538,120; 7,485,627; 7,465,444; 7,449,176; 7,417,037; and 7,354,910).

One example of a model is the IL-10-/- mouse. It has been known for some years that interleukin-10 (IL-10) affects the growth and differentiation of many hemopoietic cell types in vitro and is a particularly potent suppressor of macrophage and T cell functions. One way this was shown was by creating an IL10-/- mouse (Kuhn R et al., 1993, Cell 75:263-74). In these mice, lymphocyte development and antibody responses are normal, but most animals are growth retarded, anemic, and suffer from chronic enterocolitis. Alterations in the intestine include extensive mucosal hyperplasia, inflammatory reactions, and aberrant epithelial expression of major histocompatibility complex (MHC) class II molecules. In contrast, if these IL-10 mutants are kept under specific conditions, they develop only localized inflammation (limited to the proximal colon). It was therefore concluded that (1) bowel inflammation in these mutants originated from uncontrolled immune responses stimulated by enteric antigens; and (2) IL-10 is an essential (negative) regulator in the intestinal tract. IL 10-/- mutant mice are an accepted animal model for studying IBD.

Experimental methods comprise using four groups of mice. Two groups are fed 8 logs of an *E. coli* K12 strain expressing pPic; two groups are fed the same *E. coli* K12 strain not expressing pPic. One of the pPic groups are fed a commensal *E. coli* strain previously shown to cause colitis in the IL-10-/- mouse; one of the K12 control groups are similarly fed the commensal strain. These four groups are then followed for development of colitis, which is quantified by methods known to one of ordinary skill in the art. Following the above protocol, only the group fed commensal *E. coli* develops colitis, but this colitis is significantly diminished in the group fed *E. coli* K12 expressing Pic prior to feeding of the commensal *E. coli* strain.

These experiments are performed in collaboration with Drs. Sandra Kim and Balfour Sartor and are performed at the NIH-supported NGRRC, at the University of North Carolina in Chapel Hill. Each bacterial strain is streaked on MacConkey agar from frozen glycerol stocks and incubated for 24 hours. A single colony is subcultured to 10 ml brain heart infusion (BHT) broth, and incubated to mid-log phase. Four groups of 10-12 week old previously germ-free IL 10-/- 129S6/SvEv mice (n=8 mice/group) are mono-associated by oral gavage with 10.sup.8 CFU of the *E. coli* strain. Bacterial association and the absence of contamination by other bacterial species is confirmed by fecal culture. Four mice from each group will be euthanized at 3 and 7 weeks, correlating with previous studies that showed mice mono-associated with *E. coli* developed moderate to severe colitis by 3 weeks; the later time point correlates with previous studies performed by Drs. Kim and Sartor utilizing a known colitogenic murine *E. coli* strain, NC101. Tissue sections from the duodenum, jejunum, ileum, cecum, colon and rectum are fixed in 10% neutral buffered formalin for 18 hours, transferred to 70% ethanol, embedded in paraffin, and either stained with hematoxylin and eosin (H&E) for histology or unstained for fluorescence in situ hybridization (FISH). H&E sections are scored in a blinded fashion by a single investigator using a validated scale. To provide quanititative data on inflammation, intestinal tissue sections are incubated for 24 hours in cell culture medium, followed by quantitation of spontaneous IL-12/23p40 secretion by ELISA using methods known to those of ordinary skill in the art. The myeloperoxidase (MPO) assay is performed to permit quantitation of PMN-induced inflammation. Luminal bacterial concentrations are quantitated by culturing serial dilutions on MacConkey agar plates. Each mouse has multiple sites sampled, there are two time points, and three readouts of inflammation. To accept the hypothesis of difference between any two constructs, it is defined beforehand that significant group mean differences are apparent ($P<0.05$ by ANOVA corrected for multiple readouts) in at least two readouts from at least two sites or time points. Based on prior experience in the facility, 8 mice/group are sufficient to establish differences with positive and negative controls, testing four groups at a time. Greater numbers can be used to confirm trends in data.

Following the above described experiment, the inventors are able to show that the exogenous administration of Pic using a bacterial strain (including, for example, an *E. coli* K12 strain expressing pPic) that expresses and secretes Pic is able to treat IBD.

Example 3

Airway Inflammation

Various models of airway inflammation are used to determine whether or not a particular intervention is efficacious. Such models and experimental designs are known in the art (see, for example, US Patent Application Publication Nos. 20090274696; 20090191133; 20080172751; 20080152623; 20080064746; 20070183983; and U.S. Pat. Nos. 7,585,968; 7,256,172; 7,214,380; 6,994,870; and 5,962,445).

An example of a model used comprises using a microbe known to cause airway inflammation (i.e., a challenge model). Airway inflammation is induced by inoculation of *Pseudomonas aeruginosa* in the lung of a mouse. The mice are administered purified, Pic and the Pic S258A mutant (inactive Pic) at a dose of 5 mcg to determine if inflammation due to *P. aeruginosa* can be inhibited. Administration of these proteins is by aerosolization and is on the day of infection. The experiment is performed essentially as described above. Pic and Pic S258 is administered by aerosol device. Mice receive the aerosol mist containing 5 mcg in 0.1 ml normal saline; mice are anesthetized during aerosol administration. At the conclusion of the experiment, mice are euthanized and inflammation scored by histopathology and MPO assay.

*P. aeruginosa* (strain PA01), grown to mid-logarithmic phase in Luria-Bertani, is harvested by centrifugation at 3400×g for 15 min. After washing in pyrogen-free 0.9% NaCl (2×) and suspension of the bacteria in 10 ml of 0.9% NaCl, the number of bacteria is determined by serial dilution in sterile isotonic saline and cultured on blood agar plates. Mice are lightly anesthetized by inhalation of isoflurane (Abbott Laboratories), after which 50 µl of the bacterial solution, containing $10^8$ (or in one experiment $10^7$) CFUs is administered intranasally. Mice are anesthetized with ketamine (Eurovet Animal Health) and medetomidine (Pfizer Animal Health) after 6 hours and 24 hours and analysis is performed. In different experiments, Pic and Pic S258A are given either before, during, or after inoculation with *Pseudomonas aeruginosa*, in which case it is determined that Pic can completely or partially prevent airway inflammation and can completely or partially inhibit airway inflammation.

Following the above described experiment, the inventors are able to show that the exogenous administration of a Pic is able to treat airway inflammation.

Example 4

Targeting of a Broad Range of Human Leukocyte Adhesion Molecules by a Serine Protease Autotransporter from *Shigella flexneri* and Pathogenic *E. coli*

The serine protease autotransporters of the Enterobacteriaceae (SPATEs) constitute a group of proteases secreted by pathogenic gram negative bacteria through the autotransporter (AT) pathway. As indicated above, the present inventors previously classified SPATE proteins into two classes: cytotoxic (class-1) and non-cytotoxic (class-2). Here, the inventors show that Pic, a class-2 SPATE protein produced by *Shigella flexneri* 2a, uropathogenic and enteroaggregative *E. coli* strains targets a broad range of human leukocyte adhesion proteins. The substrate specificity was highly restricted to glycoproteins rich in O-linked glycans including CD43, CD44, CD45, CD93, CD162 (PSGL-1) and the surface attached chemokine fractalkine, all of them implicated in leukocyte trafficking, migration and inflammation. N-terminal sequencing of cleaved products identified Pic cleavage sites between Thr or Ser and the preceding residue. The O-linked carbohydrate sLewis-X implied in inflammation and malignancy was able to block Pic protease activity. Exposure The serine protease autotransporters of the Enterobacteriaceae (SPATEs) constitute a group of proteases secreted by pathogenic gram negative bacteria through the autotransporter (AT) pathway.

Here, the inventors show that Pic, a class-2 SPATE protein of human leukocytes to purified Pic resulted in impairment of neutrophil chemotaxis and transmigration, as well as substantial PMN activation. Moreover, Pic-treated T cells underwent programmed T cell death. The Pic-related protease known as Tsh/Hbp, implicated in extra-intestinal infections, exhibited a similar proteolytic spectrum. The class-2 SPATEs represent a novel class of immune-modulating bacterial virulence factors.

Reagents, Recombinant Proteins and Antibodies.

Recombinant human IL-8 and fMLP (formyl-Methionyl-Leucyl-Phenylalanine) were obtained from BD Biosciences. SLewis X carbohydrate was obtained from CalBiochem. Glycosylated recombinant proteins were obtained from R&D Systems as follows: CD44 (Accession #P16070), CD45 (Accession #P08575), PSGL-1 (Accession #NP002997), Fractalkine (Accession #P78423), E-selectin (Accession #P16581), P-selectin (Accession #P16109), L-selectin (Accession # P14151). Mac-1/Integrin αMβ2 (Accession #NP_001139280), ICAM-1 (Accession # P05362).

Antibodies used in immunoblots included CD44 (sc-7946, SantaCruz B.), CD43 (MHCD4300, Invitrogen), CD45 (MHCD4500, Invitrogen), CD162/PSGL-1 (556053, BD), Fractalkine (sc-74015, SantaCruz B.), anti-sLewisX (565953 Calbiochem), Mac-1 (FAB1730F, R&D sys), ICAM-1 (BBA17, R&D sys), Lamp-1 (sc-17768 SantaCruz B.) and Lamp2 (sc-5571, SantaCruz B.).

Antibodies against the extracellular domain of glycoproteins used in flow cytometry experiments included: FITC-CD93 (551531, BD), PE and FITC-CD15s (sc-32243 and sc-32243, SantaCruz B.), PerCP-Cy5.5 CD62L (Biolegends), FITC-anti-human IgG (sc-2456, SantaCruz B.), APC-CD44 (17-0441-83, e-Biosciences), PE-CD45RO (555493, BD), PE-CD43 (MHCD4304, Invitrogen), APC-CD43 (MHCD4305, Invitrogen), PE-CD16b (550868, BD), PE-CD4 (555347, BD), PE-PSGL-1 (556055, BD), Alexa700-CD16 (302026, Biolegend), FITC-CD14 (347493, BD) and CD99 (FAB3968F, R&D Sys), APC-Cy7-CD3 (557757, BD), PE-Cy7-CD56 (557747, BD) and Biotin-CD8 (555365, BD).

Bacterial Strains, Growth Conditions and Supernatant Obtention

Strains *S. flexneri* 2457T and EHEC 042 were previously described (Nataro J P, Deng Y, Cookson S, Cravioto A, Savarino S J, Guers L D, Levine M M, & Tacket C O (1995) *J Infect Dis* 171, 465-468.). Bacterial strains and their isogenic Pic mutants were cultured overnight at 37° C. in LB broth, diluted 100-fold in fresh LB, and cultured with constant agitation for 4 h (OD600 nm=1.0-1.2). Bacterial supernatants were then passed through a 0.22 µm pore-size filter and concentrated 100× in 100 kDa cutoff centricon-70 molecular filters (Millipore), washed twice with PBS in the same filters and saved at −80° C. until their used.

Purification of Pic, PicS258A, Tsh, SepA and SigA Proteins.

SPATE proteins were purified from *E. coli* HB101 harboring minimal clones as previously reported (Dutta P R, Cappello R, Navarro-Garcia F, & Nataro J P (2002) *Infect Immun* 70, 7105-7113.). Anion-exchange purified proteins were treated with Endo-Trap-Blue (Lonza) to remove LPS accordingly to the manufacturer's specifications, dialyzed in 1× PBS pH 7.0 and stored in small aliquots at −80° C.

Preparation of PMNs and PBMCs.

Heparinized blood from healthy human donors was mixed with dextran/0.9% NaCl (final concentration, 1.5% dextran) and allowed to settle undisturbed for 30 minutes. The leukocyte-rich plasma was layered over a histopaque 1077 density gradient (Sigma)) and centrifuged at 400× g for 30 min. PBMCs were separated from the upper interface of histopaque 1077, washed twice with HBSS buffer and resuspended at $1.0 \times 10^7$ cells/ml in HBSS/Ca++/Mg++ buffer (Gibco). The cell pellet containing PMNs and erythrocytes was treated with hypotonic lysis buffer and washed with HBSS buffer without Ca++/Mg++. The preparation contained ~95% neutrophils, as judged by morphological examination, and cells were >90% viable as determined by trypan blue dye exclusion. PMN were washed and resuspended in HBSS buffer without Ca++/Mg++ at $1\times10^7$ cells per ml (Gibco), PMN were used within 2 hr of venipuncture. PMNs used in this work were derived from 6 healthy donors.

For protease experiments, $10^6$ leukocytes per ml were routinely treated with 0.2 µM of Pic, PicS258A or other SPATE proteins at 37° C. for 30 minutes-1 h in 5% $CO_2$ atmosphere. When working with glycosylated human recombinant proteins; 5-10 µg of CD44, CD45, PSGL-1, Fractalkine, ICAM-1, Mac-1, CD62E, CD62P and CD62L were treated with 2 µM of SPATE protein, at 37° C. for 1 h.

N-Terminal Sequence Determination.

Degradation products from digestion of O-glycoproteins were blotted onto PVDF membranes (BioRad) and stained with Coomassie brilliant blue R-250 (BioRad). Bands of interest were excised and subjected to Edman N-terminal sequencing by using an Applied Biosystems Procise 494 protein sequencer at the CVID Proteomics Biocore facility, University of Maryland at Baltimore.

Western Immunoblotting.

Degradation reactions were boiled with sample loading buffer containing 2% SDS and 10 mM DTT and analyzed in 4-20% SDS-PAGE gels (BioRad). Proteins were transferred onto nitrocellulose membranes (Millipore, Bedford, Mass.) and then blotted with the appropriate monoclonal antibodies (See the Reagent section). Bands were detected with Amersham ECL Plus Western blotting detection reagent (GE Healthcare) or TMB membrane substrate (Thermo Scientific).

Flow Cytometry.

Primary human leukocytes incubated with SPATE proteins were stained by incubation with 10 mg/mL of dye-conjugated antibodies specific to the extracellular domain of human glycoproteins and control proteins (See Reagent section). PMNs were incubated with human IgG before staining to block Fc receptors. Neutrophils were gated on the basis of low forward-scatter and high side-scatter using the anti-CD16 and CD16b antibodies. Lymphocytes were gated on the basis of low forward-scatter and low side-scatter using a monoclonal antibody against CD3. Signals were acquired with a MoFlow flow cytometer/cell sorter system (Coulter, Fla., USA) and analysis software WinList 6.0 (Verity Software House, Topsham Me. 04086).

P-Selectin-Binding Assay $0.5-1\times10^6$ leukocytes treated with SPATE proteins or PBS vehicle control were washed twice with HBSS/Ca++/Mg++ buffer and resuspended in 100 µl of the same buffer. Subsequently, cells were incubated with 10 µg of P-Selectin-Fc chimera (R&D systems) for 30 min at 4° C., washed once, and resuspended in 100 µl of HBSS/Ca/Mg buffer containing FITC-labeled goat anti-human IgG (2 µg/ml, SantaCruz Biotech). After incubation for another 30 min at 4° C., cells were washed twice and 10,000 cells were collected for flow cytometric analysis with a MoFlow flow cytometer/cell sorter system (Coulter, Fla., USA).

Neutrophil Transendothelial Migration Assay

Transmigration assays were performed according to previously described techniques. Briefly, human lung microvascular endothelial cells (HBMVEC-L, ATCC, Manassas, Va.) were seeded on collagen coated inserts (diameter, 6.5 mm; pore size, 3 µm (Becton Dickinson) at a concentration of $2.5\times10^4$ cells/insert in 300 µl of HEC-C1 medium. The inserts were then placed in a 24-well plate, each well of which contained 500 µl medium, and cultured until the monolayers were confluent (approximately 3-4 days). The luminal (apical) and abluminal (subendothelial) compartments were generated in the upper and bottom chambers, respectively. 300 µL of serum-free RPMI medium containing calcein-stained human PMN cells ($3\times10^5$) with Pic, PicS258A or PBS vehicle control were added to the upper chamber, whereas 100 mM of IL-8 (BD Biosciences) or 100 nm of fMLP (BD Biosciences) were added to the lower chamber. Cells were allowed to migrate for 4 h. After incubation, neutrophils that migrated into the lower chamber were collected for counting with a fluorometer (Fluoroskan Ascent, Thermolab Sys.), and the percentage of cells that migrated with or without chemoatractant was determined. Data were reported in means and S.E.M. of three or more independent experiments performed in triplicate, which were combined and analyzed by one-way ANOVA.

Chemotaxis Assay.

Chemotaxis assays were performed as in transmigration assays (without cell monolayer) and as previously described. 300 µL of serum-free RPMI medium containing calcein-stained human PMN cells ($3\times10^5$) with Pic, PicS258A or PBS vehicle control were added to the upper chamber of Fbg-coated transwell inserts, whereas 100 mM of IL-8 or 100 nM of fMLP were added to the lower chamber. Cells were allowed to migrate for 4 h. After incubation, neutrophils that migrated in the lower chamber were collected for counting with a Fluoroskan fluorometer, and the percentage of cells that migrated with or without chemoatractant was determined. Data were analyzed likewise transmigration assays.

PMN Oxidative Burst Determination.

PMNs were incubated with dihydrorhodamine 123 (DHR) for 5 minutes and treated with 0.2 µM of SPATE protein or stimulated with Phorbol 12-Myristate 13-Acetate (PMA). Dihydrorhodamine oxidation was measured by flow cytometry. All experiments were performed in three independent experiments using cells from three different donors. Results were reported as the percentage of cells undergoing oxidative burst normalized against cells treated with vehicle control.

Annexin-V Binding/Propidium Iodide Assay.

Apoptosis induced by Pic cleavage of glycoproteins on activated T lymphocytes was determined according to the protocol previously published (Chen S C, Huang C C, Chien C L, Jeng C J, Su H T, Chiang E, Liu M R, Wu C H, Chang C N, & Lin R H (2004) *Blood* 104, 3233-3242.). T cells were activated with 2 µg/mL ConA for 48 hours, washed with HBSS buffer and cultured in Dulbecco modified Eagle (DMEM) complete medium containing IL-2 (100 U/mL) for three more days. At day five, activated T cells were harvested and incubated with PBS vehicle or Pic (0.2 µM), PicS258A (0.2 µM), anti-CD3 (1 µg/mL) plus anti-CD28 (1 µg/mL) for 6 hours at 37° C. Cell death was measured with Annexin-V staining and propidium iodide by flow cytometry.

Statistical Analysis

Experimental data were expressed as mean±SEM in each group. Results from three or more independent experiments performed in triplicates were combined and analyzed by one-way analysis of variance (ANOVA) using Prism with Bonferroni post test. A P value of 0.05 was considered statistically significant.

Ethics Statement.

Blood from healthy donors were obtained under informed consent according to the Protocol ( ), approved for the University of Maryland, School of Medicine Human Subjects committee.

Results

Mucinase activity of *Shigella flexneri* and potential targets on Human Muc proteins. The inventors have previously reported the ability of the Pic protease from *E. coli* and

Figure 9A:
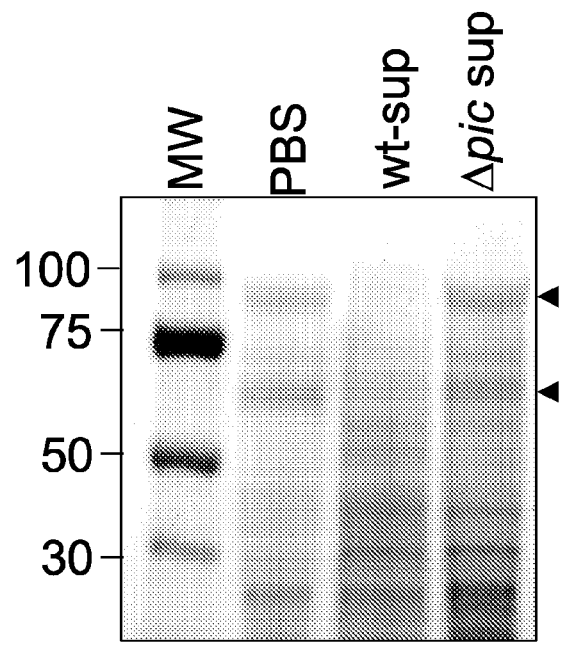
FIG. 9. Cleavage of bovine submaxillary mucin by *Shigella flexneri*. Panel A. 16 µg of bovine submaxillary mucin (BSM) were incubated with log phase supernatants from *Shigella flexneri* 2457T (wt-sup), *S. flexneri* 2457TΔpic (Δpic sup) or PBS vehicle control at 37° C. by overnight. Samples were analyzed by SDS-PAGE and blue Coomassie stain. Major mucin bands are depicted with head arrows. Panel B. 100 µg of BSM were incubated with 20 µM of purified Pic protein or PBS vehicle control for 1 h, 5 h and overnight at 37° C. Major degradation products are indicated with arrowheads in the sample corresponding to overnight incubation. Mucin degradation products numbered 1 and 2 were subjected to N-terminal sequence analysis.
Figure 9B:
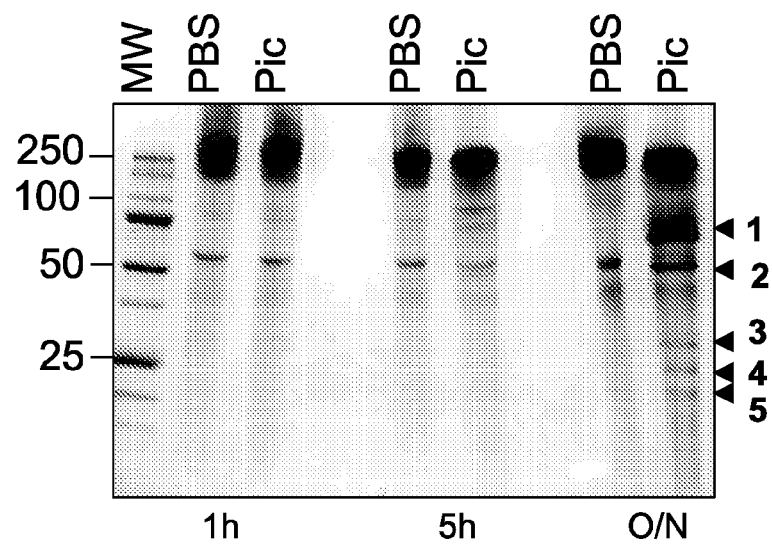

*Shigella* to cleave ovomucin and bovine submaxillarly mucin (BSM). After prolonged incubation (overnight), supernatants of *S. flexneri* 2a cause near complete degradation of the major mucin species (FIG. 9A). To gain insight into other potential targets for Pic, we sought to identify the substrate cleavage site(s). BSM was incubated with purified Pic protein for 1 h, 5 h and overnight at 37° C. (FIG. 9B). N-terminal sequencing revealed the first 8 amino acids of both fragments 1 and 2 to be SETNAIIG; this corresponded to residues $S^{588}$ and following on the 462 kDa BSM glycoprotein (Bos Taurus, XP_002687422.1).

BLAST analysis of the predicted Pic target suggested 100% identity with sequences encoding the human Muc19 protein (XP_002344701.1), the 1,184 kDa apomucin protein (NP_001106757.1), the Equinus submaxillary apomucin (XP_001915445.1) and two more human hypothetical mucin proteins (XP_002343203.1, XP_002347351.1). Interestingly, sequences similar to SETNAIIG were found within a large number of other human Muc and Muc-related proteins, suggesting the possibility that the substrate profile of Pic may be broader than we had supposed.

Cleavage of Sialomucin (CD43) on Human Leukocytes by Pic-Producing Pathogenic Strains.

Figure 10A:
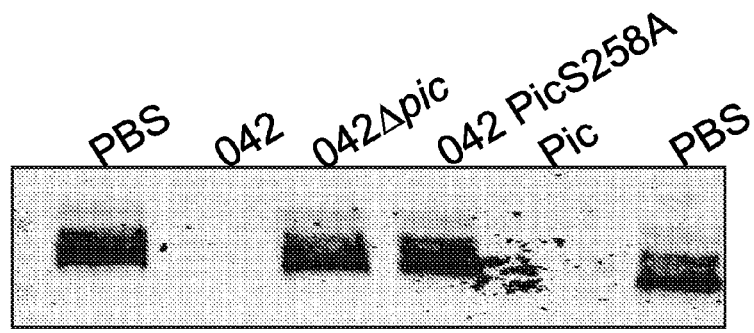
FIG. 10. Cleavage of sialomucin (CD43) on human leukocytes by Pic-producing pathogenic strains. Polymorphonuclear leukocytes (Panel A, C and E) and peripheral blood mononuclear cells (Panel B, D and F) were isolated from healthy volunteers and treated with log phase supernatants from the following strains: EAEC 042, an isogenic EAEC042pic mutant, or the protease deficient EAEC042PicS258A strain; controls comprised 2 µM of purified Pic protein or PBS (Panel A-B). Cells were alternatively treated with supernatants of wild type *Shigella flexneri* 2457T, an isogenic Pic mutant, an isogenic SigA null mutant strain, or with 2 µM of purified Pic, PicS258A or SigA (C-D). Following 30 minutes incubation at 37° C., samples were analyzed by SDS-PAGE followed by immunoblot (A-D) or flow cytometry (E-F) using an Hrp- or APC-conjugated monoclonal antibody specific to the extracellular domain of human CD43. PMBC were gated by low scatter, while PMNs were gated under high scatter. Flow cytometry data is representative of more than four independent experiments.
Figure 10B:
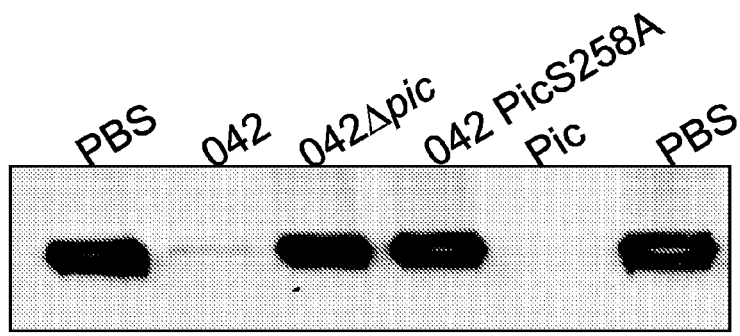
Figure 10C:
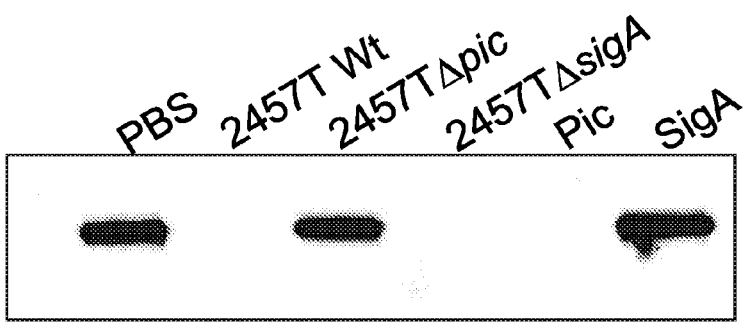
Figure 10D:
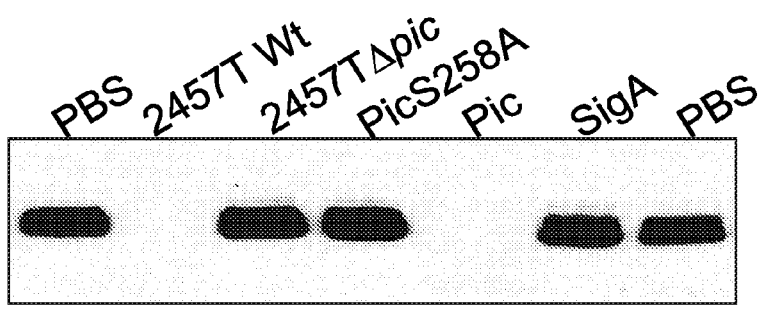

Among the mammalian Muc-related proteins are a large number of extracellular and membrane-associated glycoproteins. To determine whether Pic was capable of cleaving such proteins, the inventors first addressed CD43, also known as sialomucin, a major cell surface glycoprotein expressed on nearly all lineages of hematopoietic cells. Polymorphonuclear leukocytes (PMN) and peripheral blood mononuclear cells (PBMC) were isolated from blood samples of 6 healthy adult volunteers, and were treated with purified Pic protein, or with the supernatants of EAEC strain 042; for comparison, cells were treated with supernatants of a previously described isogenic null pic mutant, or with supernatants of 042PicS258A, which expresses Pic harboring a single amino acid mutation at the catalytic serine. As shown in FIG. 10A-B, CD43 was completely degraded by Pic on both PMNs and PBMCs, as ascertained by western immunoblot. Similar results were obtained using the supernatants of wild type *Shigella flexneri* 2457T (FIG. 10C-D).

In addition to Pic, *S. flexneri* 2457T secretes two other SPATE proteins: SepA and SigA. Neither supernatants containing SepA nor purified SigA induced any detectable degradation of CD43, suggesting that this effect is specific for the Pic SPATE (FIG. 10C-D).

Figure 10E:
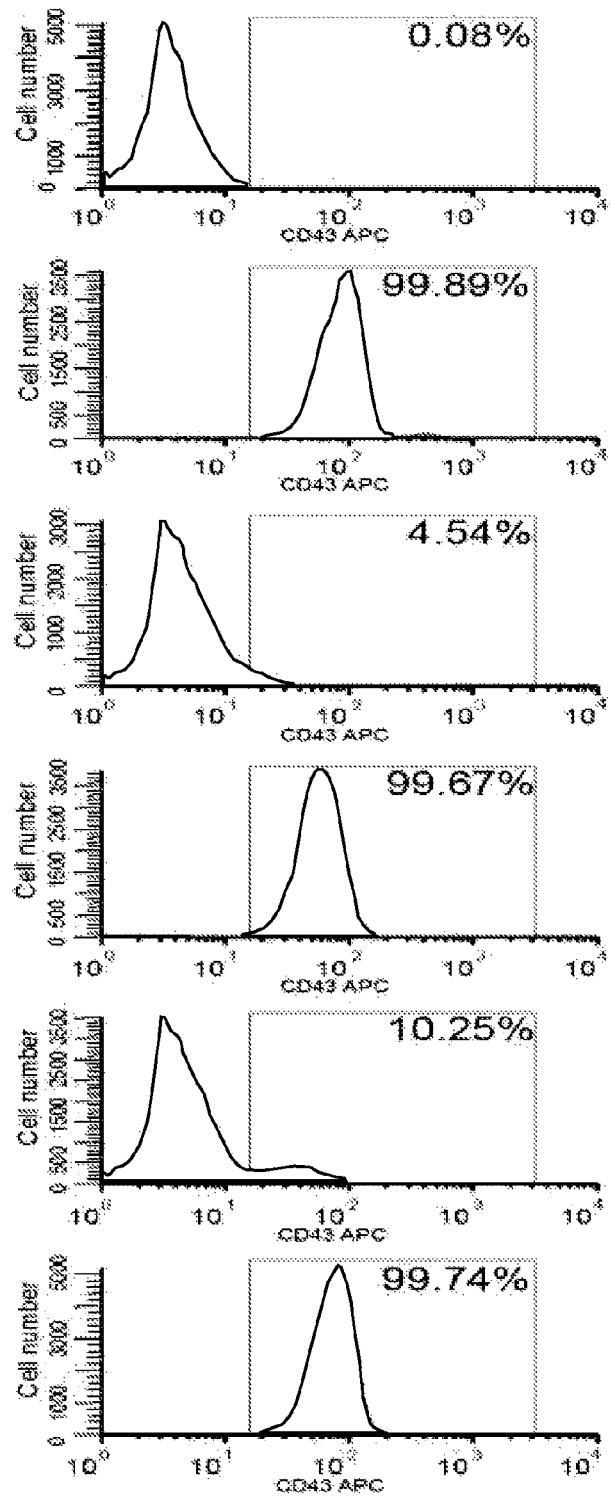
Figure 10F:
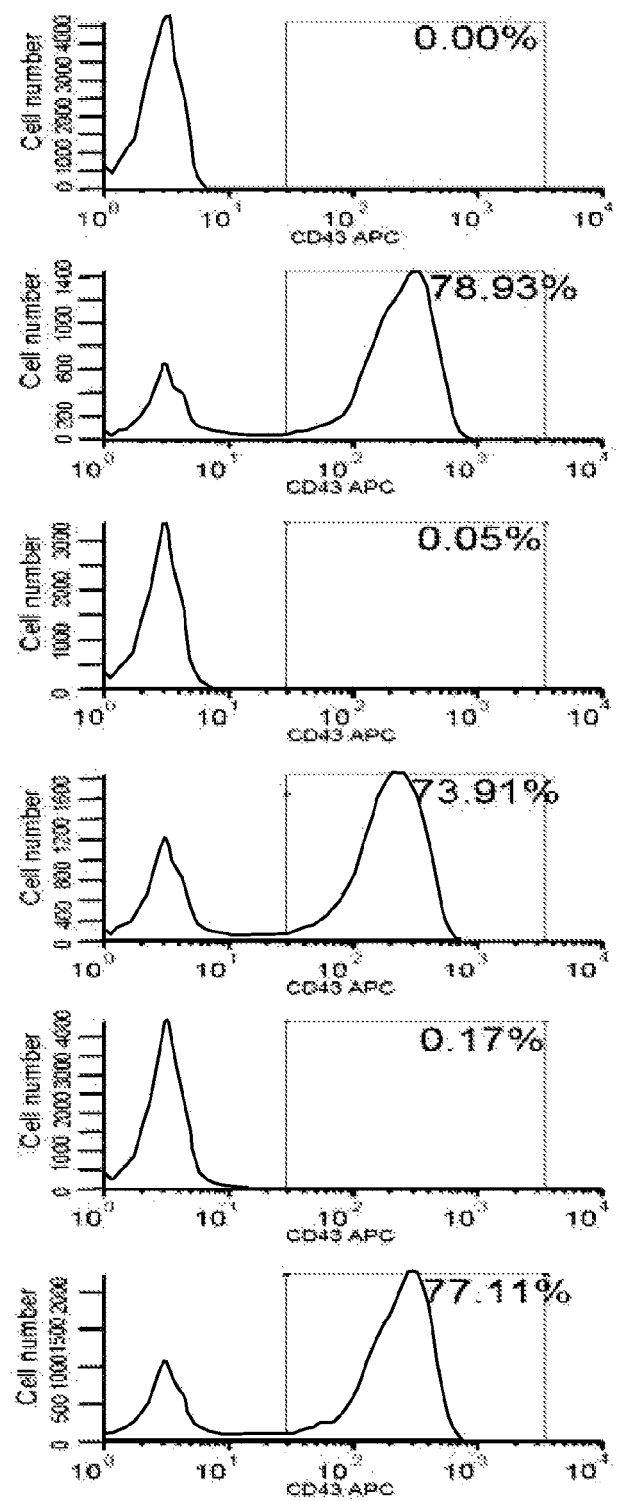

To confirm that Pic cleaves the extracellular domain of CD43 on intact leukocytes, we performed flow cytometry analyses of human PMNs or PBMCs after treatment with purified Pic, PicS258A or supernatants of *S. flexneri*. Staining with anti-CD16 (for PMNs), anti-CD3 (for lymphocytes) and anti-CD43 revealed that only CD43 was cleaved, becoming undetectable on the surfaces of both neutrophils and lymphocytes after treatment with purified Pic or *Shigella* supernants, but not after treatment with purified PicS258A (FIG. 10E, F). In similar experiments, the inventors found that Pic was able to remove CD43 from the surface of monocytes, natural killer and dendritic cells (Data not shown).

Pic Cleaves a Broad Array of O-Glycosylated Mucin-Like Proteins.

Figure 11:
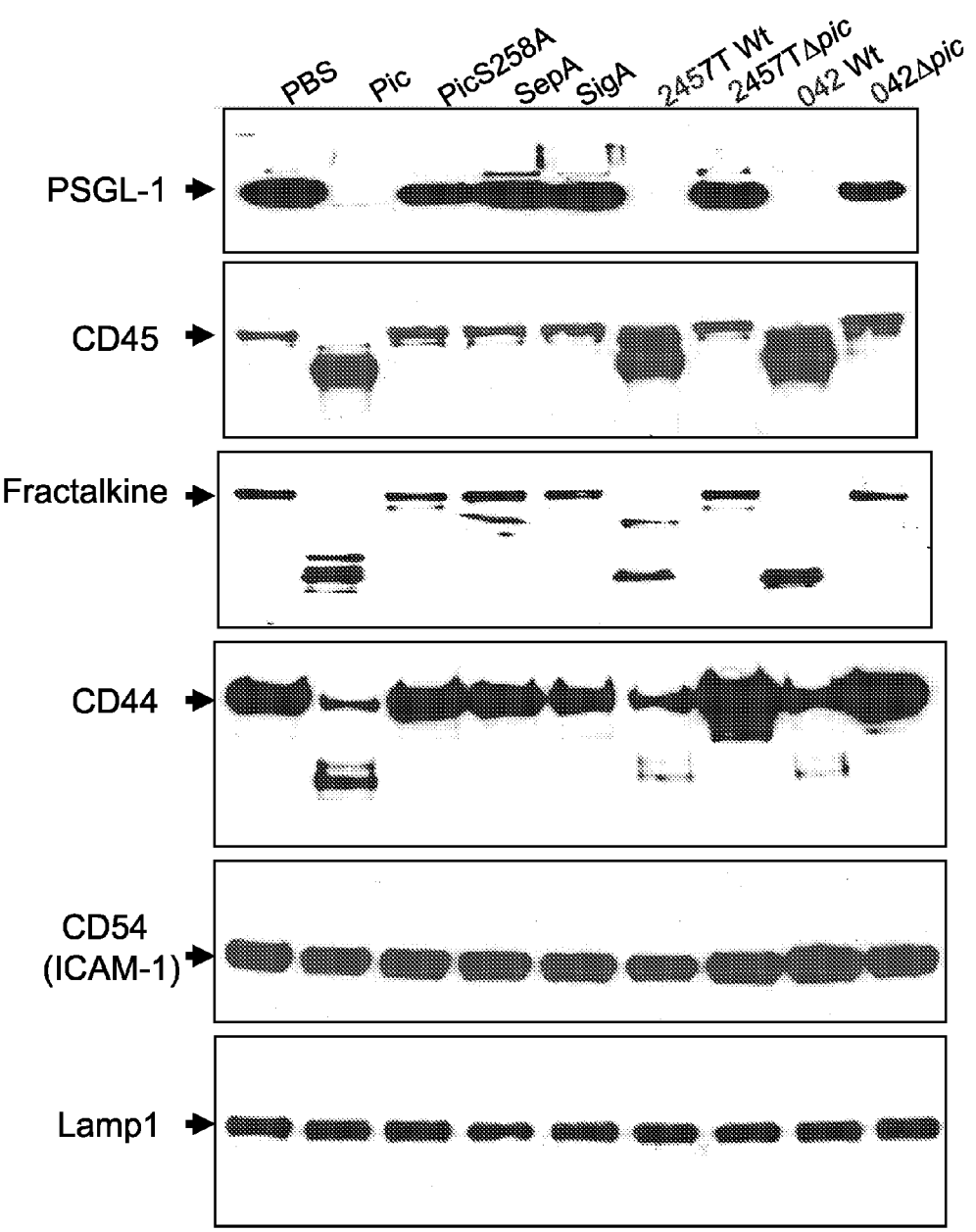
FIG. 11. Cleavage of an O-glycosylated mucin-like protein family by Pic. 5 µg of glycosylated human recombinant proteins were incubated at 37° C. for 1 h with supernatants of *Shigella flexneri* 2457T, EAEC042, the isogenic *S. flexneri*Δpic and EAEC042-pic mutant strains or with 2 µM of purified Pic, PicS258A, SepA or SigA. Samples were analyzed by SDS-PAGE and subsequent immunoblot using monoclonal antibodies to the external domain of PSGL-1, CD45, CD44 and fractalkine. Control proteins included ICAM-1 (CD54) and LAMP-1.

Having extended the substrate profile of Pic to include mucin-like leukocyte surface proteins, other members of the mucin protein family were examined for susceptibility. The inventors first addressed other mucin type O-glycans involved in diverse functions of the immune system, including the P-selectin glycoprotein ligand 1 (PSGL-1/CD162), CD44, CD45, CD93, and Fractalkine/CX3CL1. All of these targets were degraded by supernatants of wild type *Shigella* and EAEC strains and by purified Pic protein, but not by supernatants of isogenic pic mutants or purified Pic258A protein (FIG. 11). In similar experiments, two other SPATEs secreted by *S. flexneri* 2a, SepA and SigA, showed no effect on these potential substrates (Data not shown). None of the purified proteins or bacterial supernatants cleaved recombinant ICAM-1, αMβ2 (MAC1) integrin or lamp-1 proteins (FIG. 11).

Figure 12A:
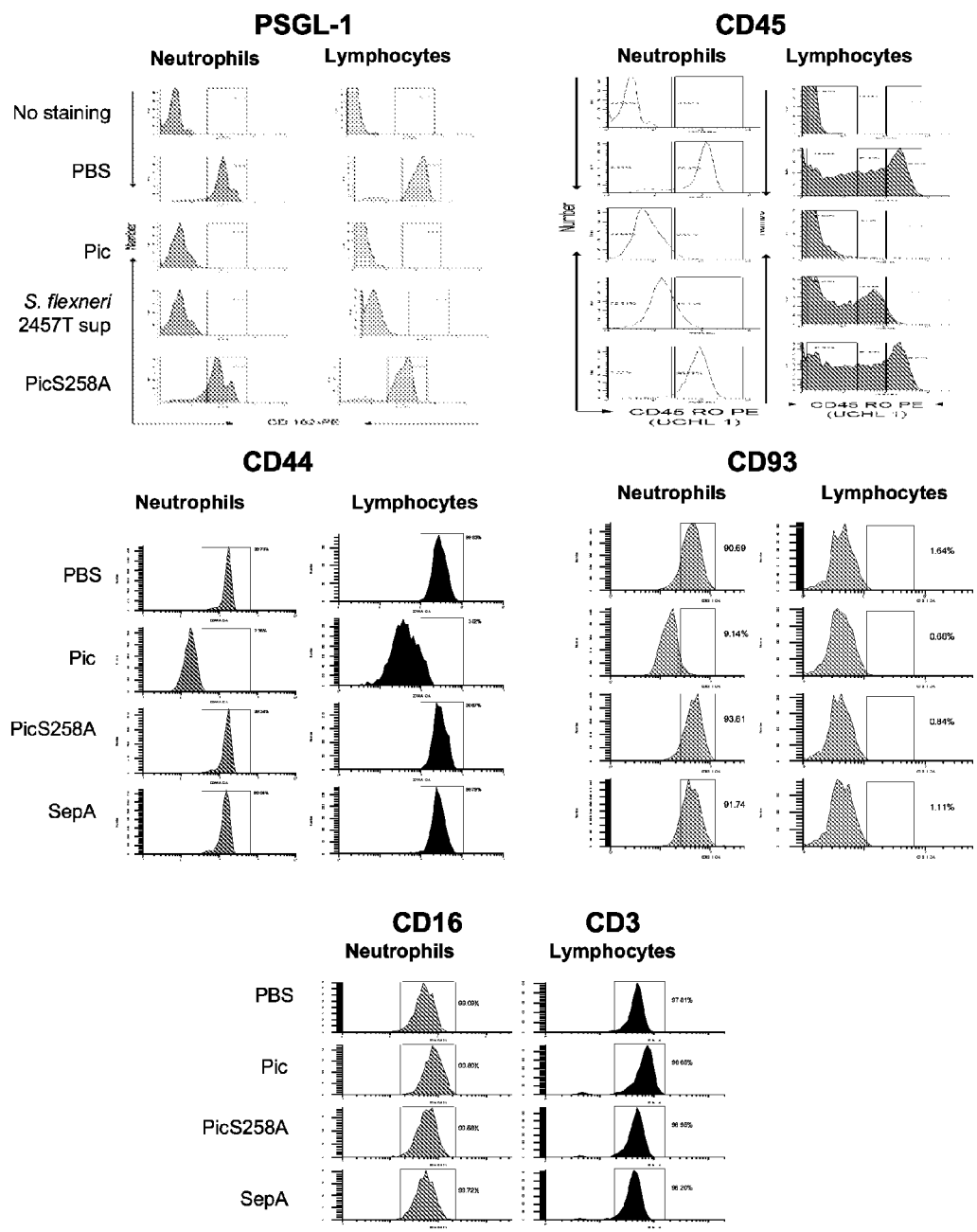
FIG. 12. Pic protein degrades the extracellular domain of O-glycosylated mucin-like proteins on human leukocytes. $1 \times 10^6$ PMNs and PBMCs were isolated from human blood and incubated at 37° C. for 30 min. with supernatants of *Shigella flexneri* 2457T and EAECO42, or with 2 µM of purified Pic, PicS258A and SepA proteins. A), Samples were analyzed by flow cytometry using monoclonal antibodies against the extracellular domains of CD44, CD45, PSGL-1, CD93, CD3 and CD 16. Lymphocytes were gated by low scatter using anti-CD3, while neutrophils were gated under high scatter and anti CD16. Flow cytometry data is representative of more than four independent experiments. B) The cleavage of PSGL-1 on human leukocytes by Pic serine protease was also visualized by fluorescence confocal micrcoscopy. After Pic treatment cells were stained for DNA, actin and PSGL-1, followed by fluorescence microsopy.
Figure 12B:
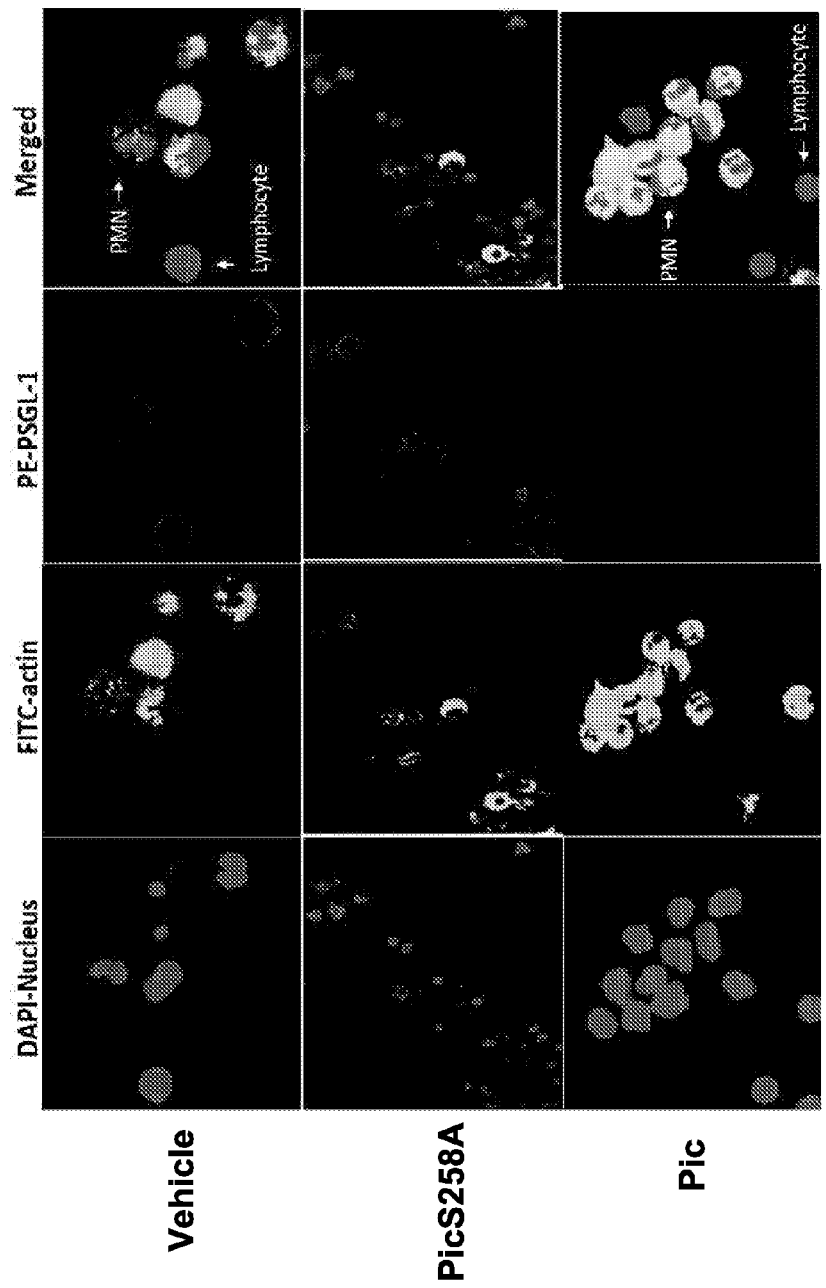
Figure 20:
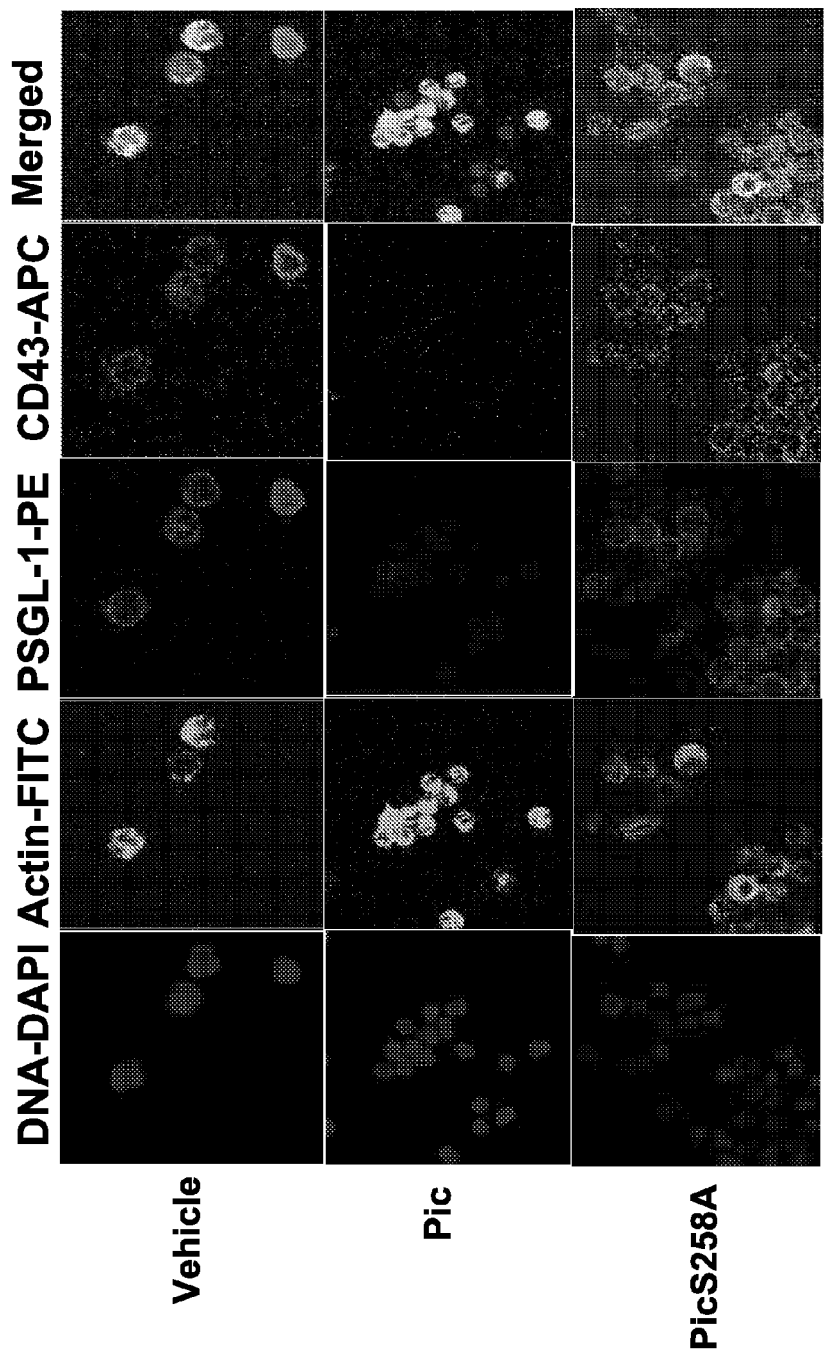
FIG. 20. Cleavage of CD43 and PSGL-1 by Pic serine protease analyzed by confocal mycroscopy. 1×10⁶ leukocytes were incubated with 2 µM of Pic, PicS258A or vehicle control for 30 min at 37° C. Cells were stained for DNA, actin, CD43 and PSGL-1, followed by fluorescence confocal microscopy analysis.

To evaluate whether Pic cleaves these diverse mucin-related targets on intact human leukocytes, we treated human neutrophils and lymphocytes with purified SPATE proteins and *S. flexneri* supernatants, and analyzed the presence of the various targets by flow cytometry, employing monoclonal antibodies that recognize the extracellular domains of each molecule. All molecules that were susceptible to cleavage in purified form were also degraded from the surfaces of human neutrophils and lymphocytes (FIG. 12). *Shigella* supernatants cleaved the extracellular domains of PSGL-1 and CD45 (FIG. 12A), whereas CD3 and CD16 were not affected (FIG. 12A). Other surface leukocyte proteins such as CD4, CD8, CD14, CD19, CD62L, CD16 and CD56 were not cleaved by *Shigella* supernants or purified Pic protein (Data not shown). The heavily O-glycosylated protein CD93, which is present on neutrophils but not on lymphocytes, was also degraded by the Pic protease (FIG. 12A). Surface distribution of CD43 and PSGL-1 after treatment with Pic proteins and vehicle control were also analyzed by confocal microscopy (FIG. 12B and FIG. 20).

Figure 21A:
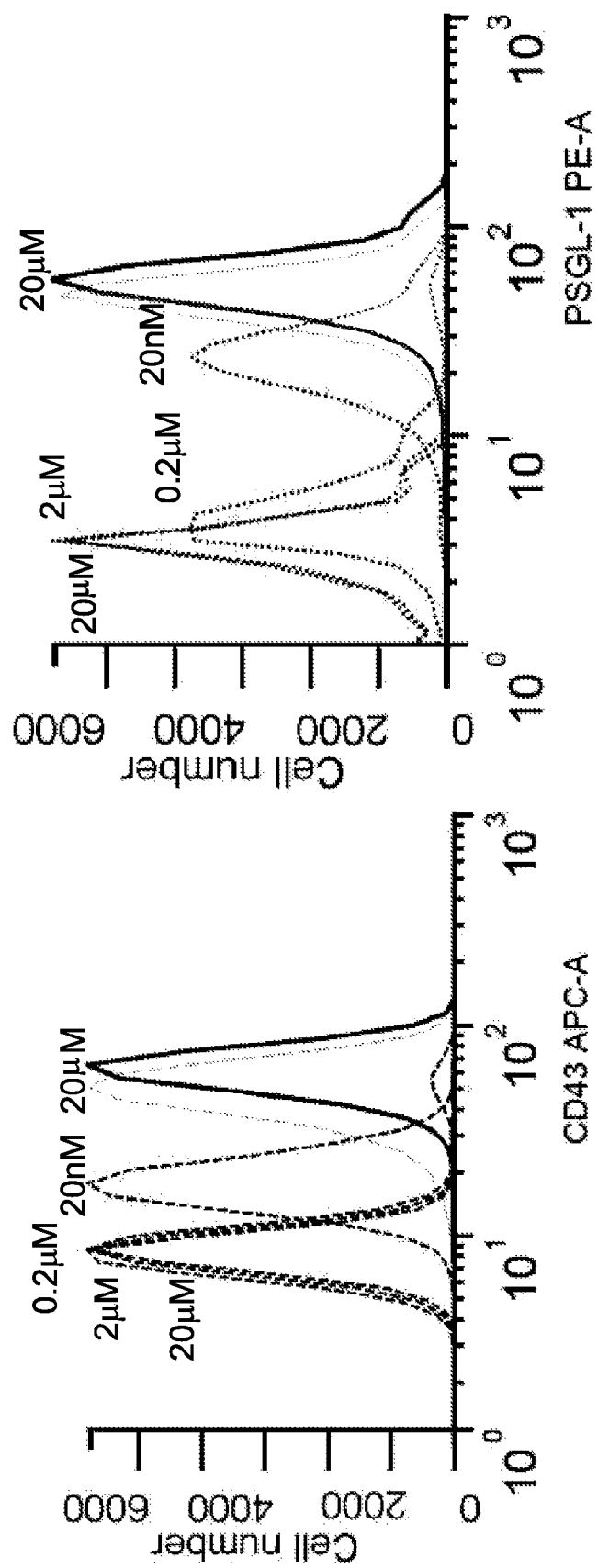
FIG. 21 Doses response effect of Pic and cell viability. 1×10⁶ PMNs were incubated with varies concentrations of Pic (20 nM-20 µM) for 1 h at 37° C. Cells were stained with ViviD, CD43-APC and PSGL1-PE antibodies, followed by flow cytometry analysis. A-Doses response effect of Pic on the depletion of CD43 and PSGL-1. B, Viability of PMNs after treatment with 2 µM of Pic, which was the concentration able to completely remove CD43 and PSGL-1.
Figure 21B:
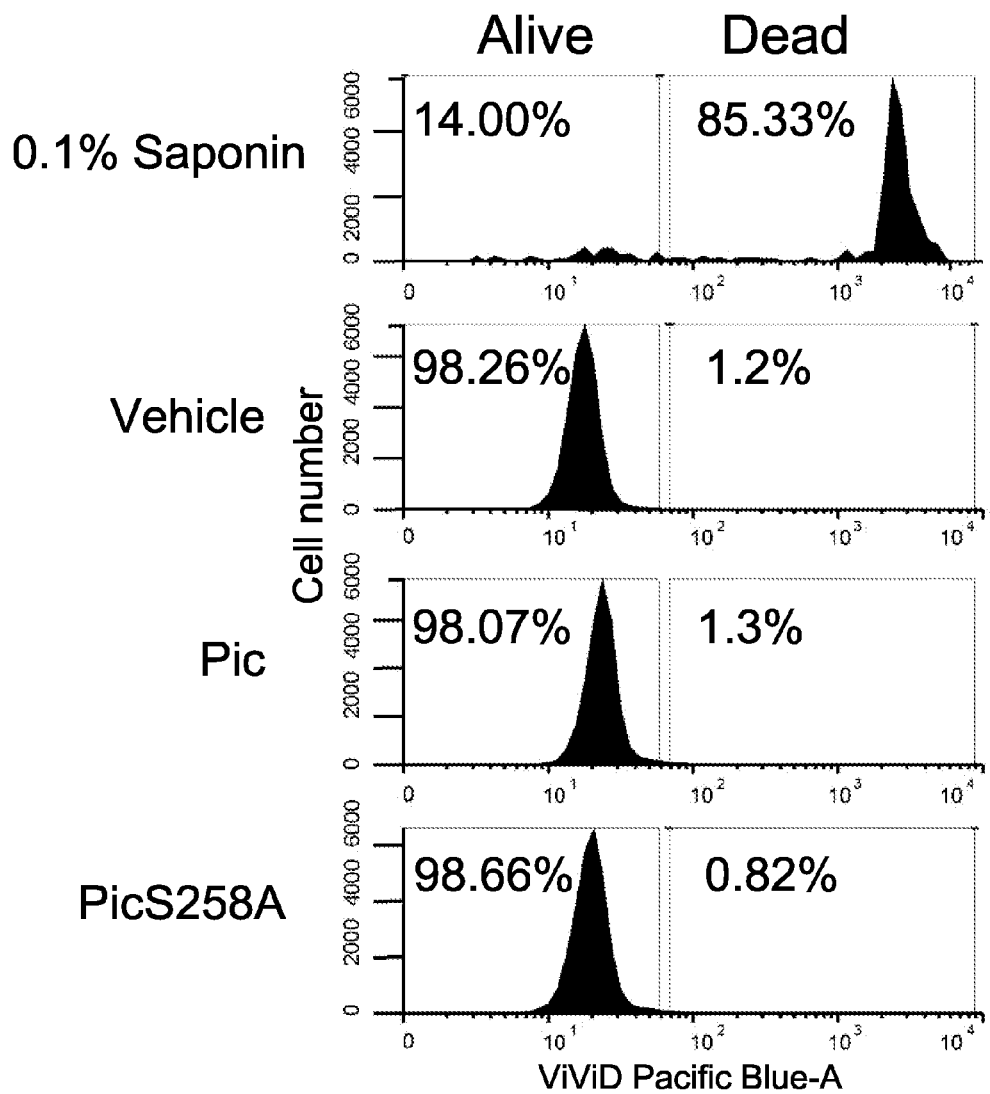

Class 1 SPATEs, such as Pet and SigA proteins have cytotoxic effects on target cells, essentially on epithelial cells. The inventors treated human polymorphonuclear cells with Pic and assessed their viability using viviD, IP or anexin dyes. These experiments revealed no significant difference in cell viability among all samples (FIG. 21).

Pic Recognizes O-, but not on N-Glycosylated Glycans.

Figure 13A:
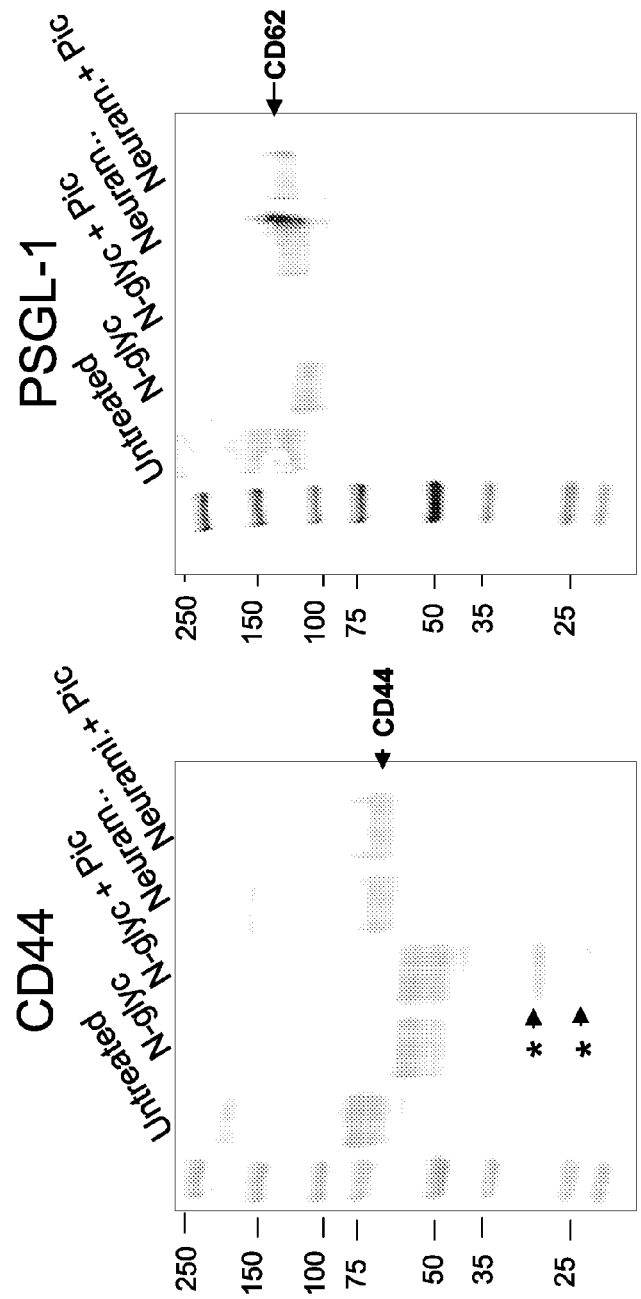
FIG. 13. Proteolytic activity of Pic is dependent on O-, but not on N-glycosylation. Panel A, 5 µg of recombinant CD44 and PSGL-1 proteins were de-glycosylated with neuraminidase or N-glycosydase F at 37° C. overnight, subsequently, de-glycosylated proteins were incubated with 2 µM of Pic at 37° C. for 1 h. Samples were analyzed by Western blot using an anti-CD44 and anti-PSGL-1 antibodies. Panel B, 5 µg of recombinant CD44, CD45, PSGL-1, ICAM-1, MAC-1 and P-selectin were incubated with PBS vehicle control, 2 µM of Pic or 2 µM of PicS258A at 37° C. for 1 h. Samples were analyzed by 4-12% SDS-PAGE and Coomassie blue stain. Intact recombinant proteins are indicated with arrows. Major cleaved products (*). Indicated by ρ are bands corresponding to Pic and PicS258A proteins. Panel C, Amino acid sequences flanking cleavage sites in seven Pic substrates.
Figure 22:
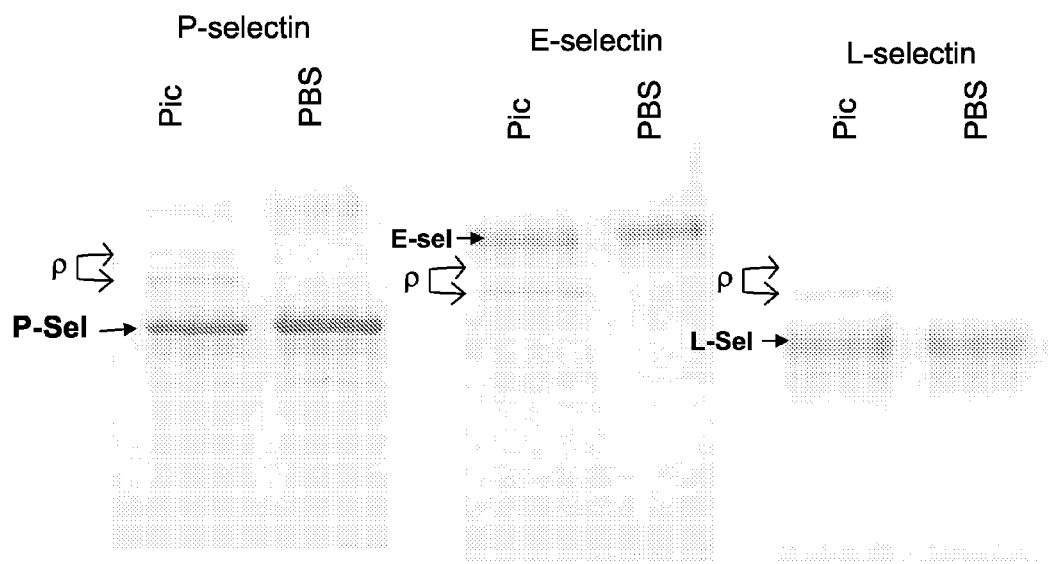
FIG. 22. Pic does not cleave Selectin proteins. 5 µg of glycosylated human recombinant P, E and L selectins were incubated with 1 µg of purified SPATE proteins for 3 h at 37° C. Samples were run by 12% SDS-PAGE and analyzed by SDS PAGE and Coomassie Blue staining. Selectin proteins are depicted with arrows. Pic, protein, which auto processes, is depicted with two arrows.

To ascertain the relevance of glycan substitution to Pic substrate recognition, human recombinant CD44 and PSGL-1, which are known to harbor both N- and O-linked oligosaccharides were employed as substrates. The present inventors found that pretreatment of the glycans with neuraminidase, which removes both N- and O-linked oligosaccharides, prevented degradation of both glycoproteins, implicating the glycans in substrate recognition (FIG. 13A). In contrast, removing N-linked saccharides with N-glycosidase-F did not protect CD45 or PSGL-1 from degradation by Pic (FIG. 13A). Compatible with this observation, Pic was not able to degrade the heavily N-linked glycosylated proteins E-, P- or L-selectins, nor the MAC-1 integrin (FIG. 13B and FIG. 22).

Figure 13B:
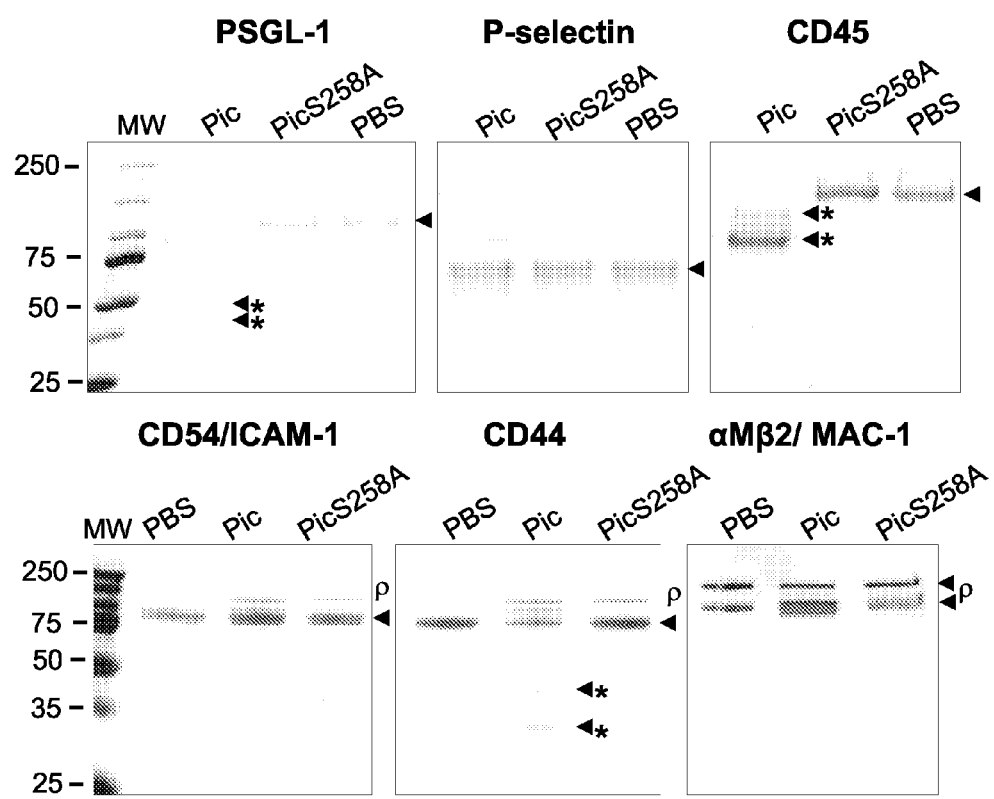
Figure 23:
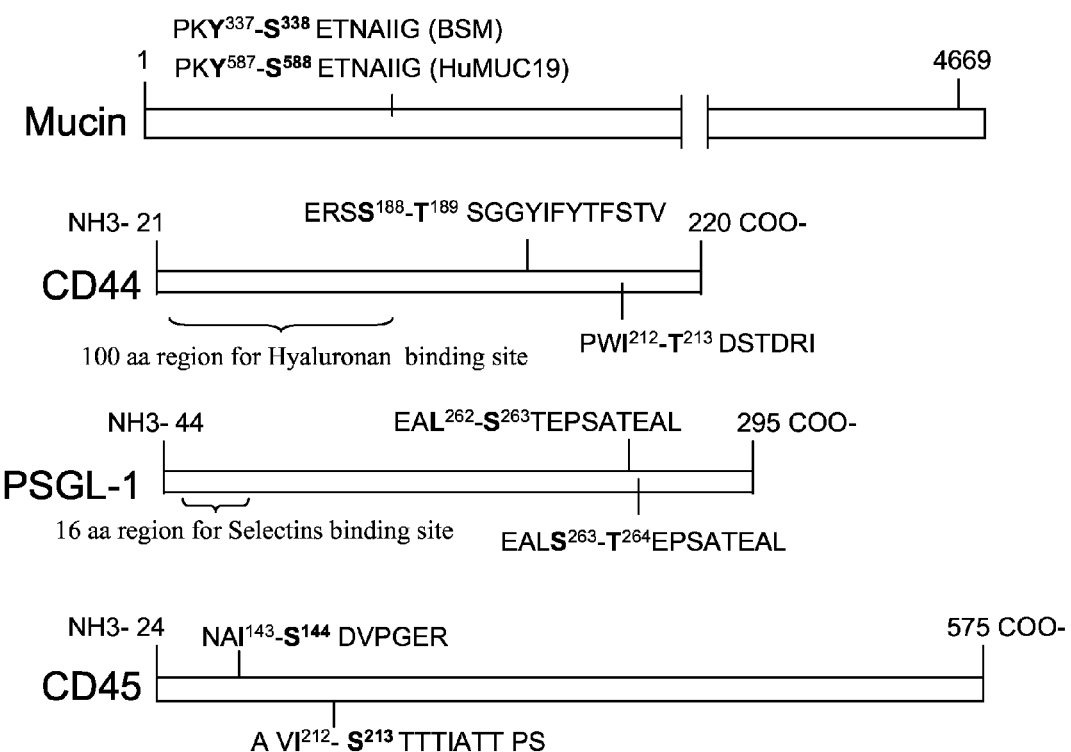
FIG. 23. Illustration of recombinant proteins depecting the corresponding Pic cleavage site on CD44, CD45 and PSGL-1 molecules. The surrounding aminoacids to the cleavage site (-), are also shown for all N-terminal sequences obtained from major cleavage products (Protein accession numbers are in material and methods section).

To assess the Pic cleavage site, recombinant PSGL-1, CD44 and CD45 were treated with purified Pic (FIG. 13B) and characterized the dominant early degradation products by N-terminal sequencing (FIG. 13B). In all cases, Pic cleaved before a serine or threonine residue (FIG. 13C and FIG. 23). Most of the putative cleavage sites occurred between Ser/Thr and aliphatic (I, V, L) or small aminoacids (A, V, S, T).

Inhibition of P-Selectin Binding to Human Leukocytes by Pic Serine Protease.

Figure 14A:
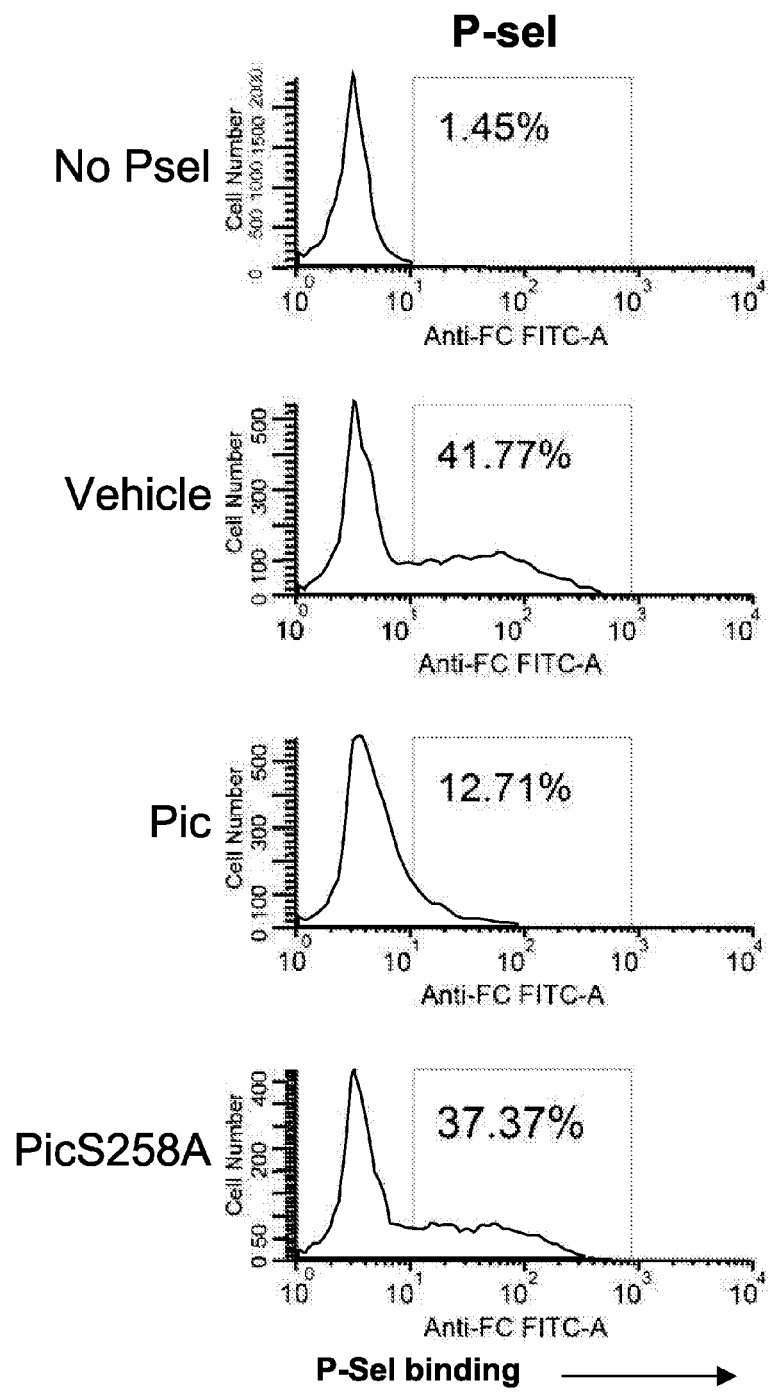
FIG. 14. Inhibition of P-selectin binding to human leukocyte by Pic. Panel A, 1×10⁶ human lymphocytes were treated with 2 µM purified Pic or PicS258A, or with PBS control for 30 min followed for 30 min incubation with human P-selectin-IgG chimera. Binding of P-selectin chimera to leukocytes was evaluated by flow cytometry using a FITC-conjugated anti-human Fc antibody. Untreated cells without incubation with P-selectin chimera (No Psel) were also stained with anti-human Fc antibody. Panel B, SLeX carbohydrate contents from cells treated with Pic, PicS258A, SepA or PBS vehicle control were measured by flow cytometry using an FITC anti-SLeX antibody (CD15s-FITC). Panel C, inhibition of Pic protease activity by SLeX carbohydrate was evaluated by Western blot employing 5 µg of recombinant PSGL-1 and 2 µM of Pic previously incubated with 2-fold increasing concentration of SLeX carbohydrate (5-1600 nM). PSGL-1 as well as PSGL-1 deglycosylated by neuraminidase treatment (De-glyc), were incubated with Pic as digestion controls. PBS, untreated PSGL-1; α-SLeX, PSGL-1 previously incubated with an anti-SLeX antibody before treatment with Pic. Western blot was developed with an anti PSGL-1 monoclonal antibody. Panel D, SLeX saccharide on PSGL-1 and deglycosylated PSGL-1 were analyzed by Western blot using an monoclonal antibody against SLeX.
Figure 14B:
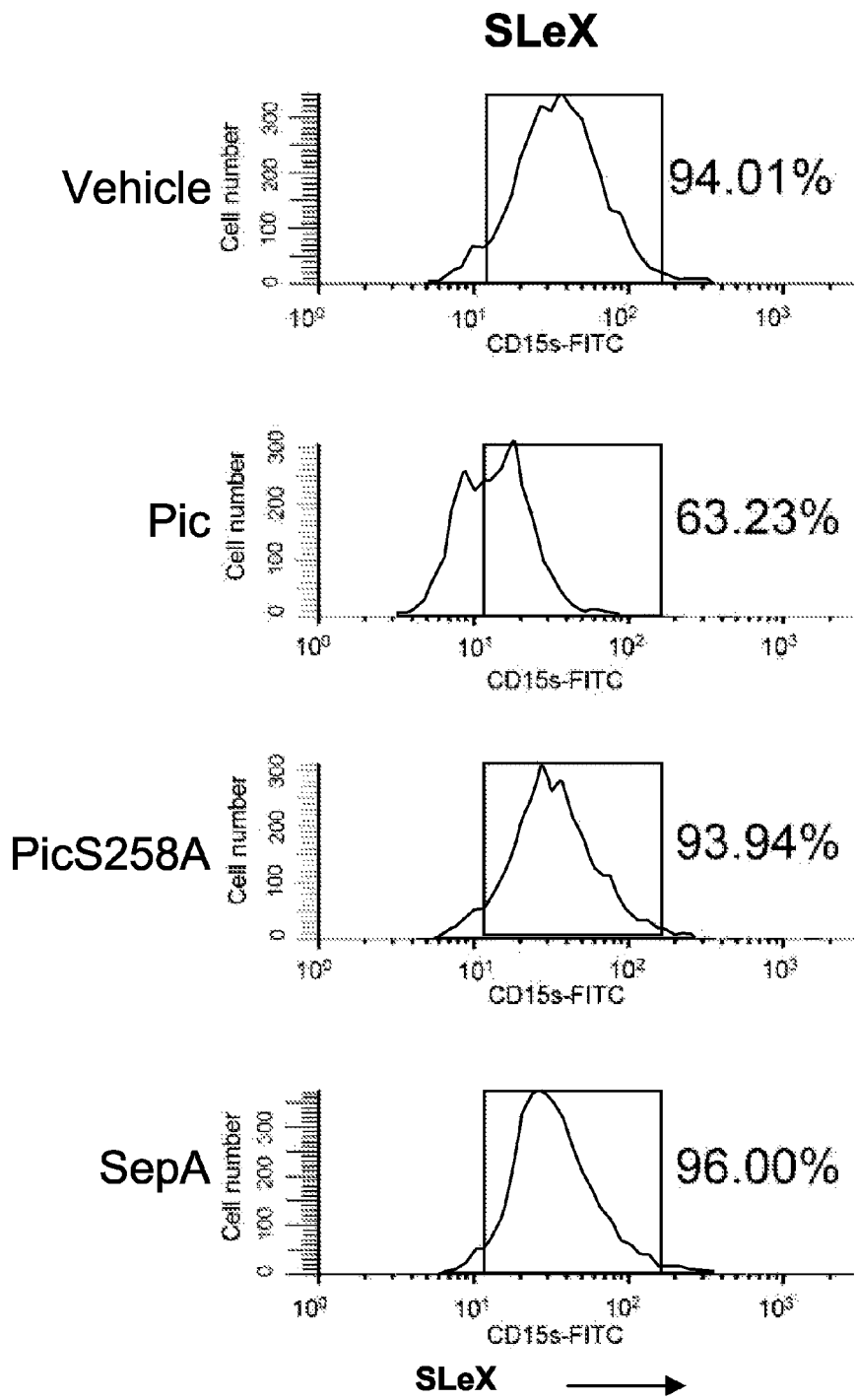

To further address the functional significance of leukocyte exposure to Pic, the inventors performed leukocyte binding assays to human P-selectin, the receptor of PSGL-1. Human neutrophils and lymphocytes were treated with purified Pic, PicS258A, or PBS vehicle control for 30 minutes, followed by incubation with human P-selectin-IgG chimera. Binding of P-selectin chimera to leukocytes was evaluated by flow cytometry using a FITC-conjugated anti-human FC antibody. The expected interaction of P-selectin with a population of untreated lymphocytes (FIG. 14A) was observed; however, only cells treated with the purified Pic protein exhibited diminished interaction with P-selectin. Rolling interactions between leukocytes and the endothelium are mediated by selectin-PSGL-1 interaction, and require branched SLewis X (SLeX)-O-glycan extensions on specific PSGL-1 amino acid residues. To evaluate if the SLeX saccharide was affected by Pic treatment, we stained human neutrophils with FITC-conjugated anti-SLeX monoclonal antibody. As shown in FIG. 14B, SLeX was found on more than 90% of the untreated neutrophils, or on cells treated with PicS258A or SepA. However, the cell population bearing the SLeX carbohydrate was reduced by almost 35% following treatment with purified Pic, when compared with untreated cells (FIG. 14B).

Figure 14C:
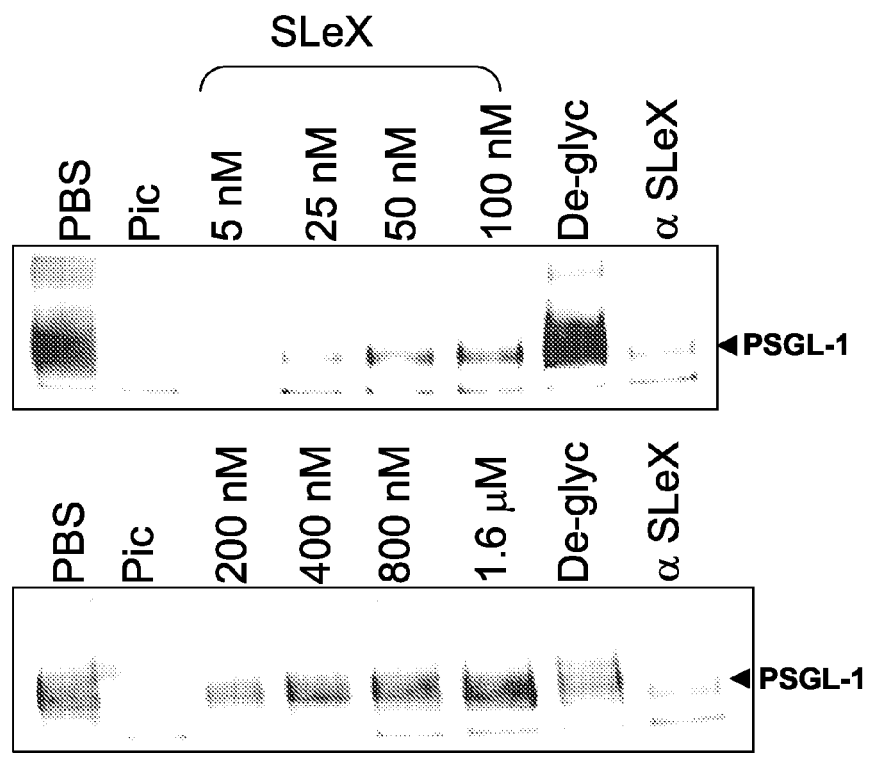
Figure 14D:
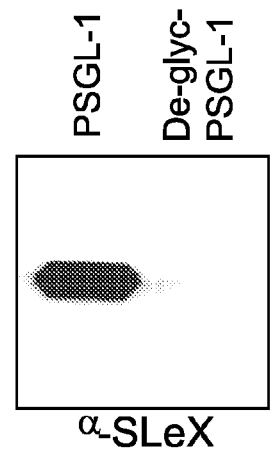

Interestingly, increasing concentrations of synthetic SLeX carbohydrate (5 nM-1.6 µM) preincubated with Pic protein before treatment of the recombinant PSGL-1 protein engendered dose-dependent inhibition of Pic protease activity on PSGL-1 (FIG. 14C). The inventors confirmed that the recombinant PSGL-1 used in the cleavage assays bears the SLeX molecule (FIG. 14D).

Impairment of PMN Chemotaxis and Transmigration by Pic.

Figure 15A:
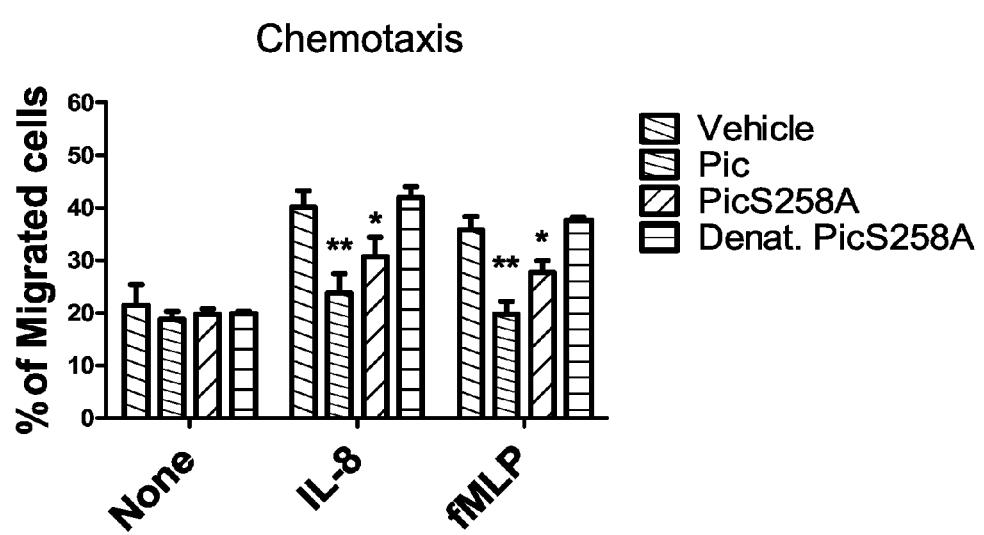
FIG. 15. Impairment of PMN chemotaxis and transmigration through endothelial cell monolayers by Pic. To assess chemotaxis responses (Panel A), 3×10⁵ calcein-AM labeled PMNs were treated with 2 µM of Pic, PicS258A or PBS vehicle control in the upper chamber of Fbg-coated transwell inserts. 100 mM of IL-8 or 100 nM of fMLP were added to the lower chamber. The movement of migratory cells through the polycarbonate membrane toward a chemoattractant underneath the membrane inserts were measured after 4 h with a fluorometer. To assess transmigration effects (panel B) calcein-AM-labeled PMNs incubated with Pic, PicS258A or PBS vehicle control were applied to the upper chamber of transwell inserts containing human lung microvascular endothelial cells (HBMVEC-L), and transmigrated PMNs were enumerated as above. Data shown are means and S.E.M. of at least three independent experiments performed intriplicate; date were combined and analyzed by one-way ANOVA. The numbers of migrated cells were normalized to vehicle control with chemoattractant (**=p<001 and *=p<0.05).

Surface glycans are implicated in a wide range of leukocyte functions. We assessed the effects of Pic on PMN function using in vitro chemotaxis assays. Calcein-labeled PMNs incubated with Pic, PicS258A or PBS vehicle control were applied on 3 µM transwells and stimulated with IL-8 or fMLP as chemoattractants; after 4 h incubation, the neutrophils that had transmigrated toward the chemoattractant were enumerated. We observed approximately 20% translocation of untreated PMNs in this model (FIG. 15A), compared with only 0-2% PMN migration when the PMNs were treated with Pic protease ($p<0.01$). Unexpectedly, the movement of PMNs incubated with the protease inactive PicS258A protein was also significantly reduced compared with buffer alone as negative control ($p<0.05$) (FIG. 15A). To determine whether this unexpected result was due to the specific action of the PicS258A protein, the protein was denatured by heating, and observed complete loss of inhibitory effects (FIG. 15A).

Figure 15B:
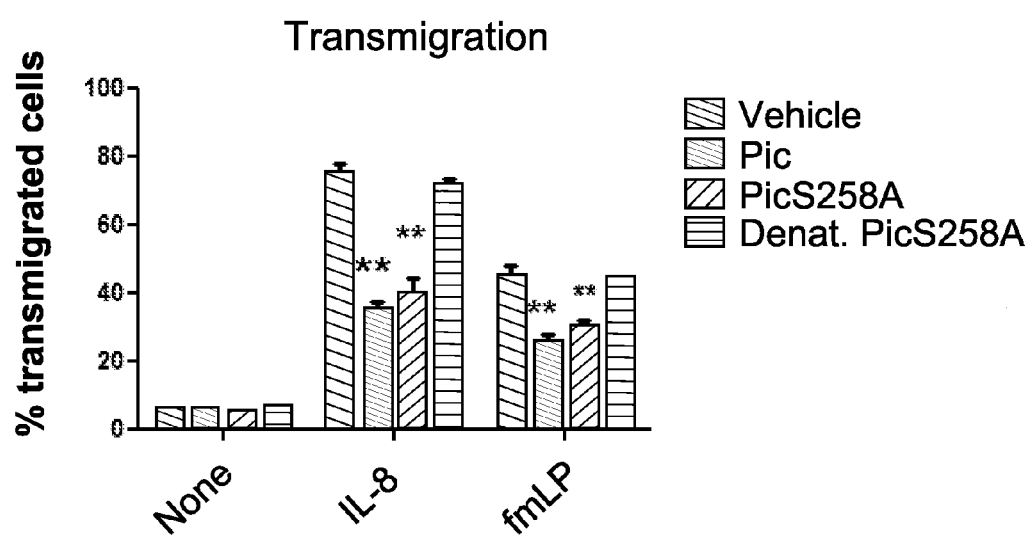

The potential effect of Pic on PMN transmigration though endothelial cell monolayers was addressed. Calcein-labeled PMNs were treated with Pic and added to HBMVEC-L monolayers cultured in transwells and stimulated with IL-8 and fMLP as chemoattractants. Untreated cells transmigrated nearly 65% and 40% in the presence of IL-8 and fMLP, respectively (FIG. 15B). In contrast, transmigration of cells treated with Pic protease in the presence of IL-8 or fMLP was approximately 31% and 21%, respectively ($p<0.01$ both treatments) (FIG. 15B). The inventors also observed a 1.5 fold-reduction of PMN transmigration when the leukocytes were incubated with PicS258A compared to untreated cells ($<0.05$) (FIG. 15B). This effect was also abolished by heat-treatment of the protease (FIG. 15B, heat PicS258A). Taken together, these data suggest that interaction of Pic with O-glycoproteins directly impairs PMN function.

Activation of Neutrophil Oxidative Burst by Pic Serine Protease.

Figure 16A:
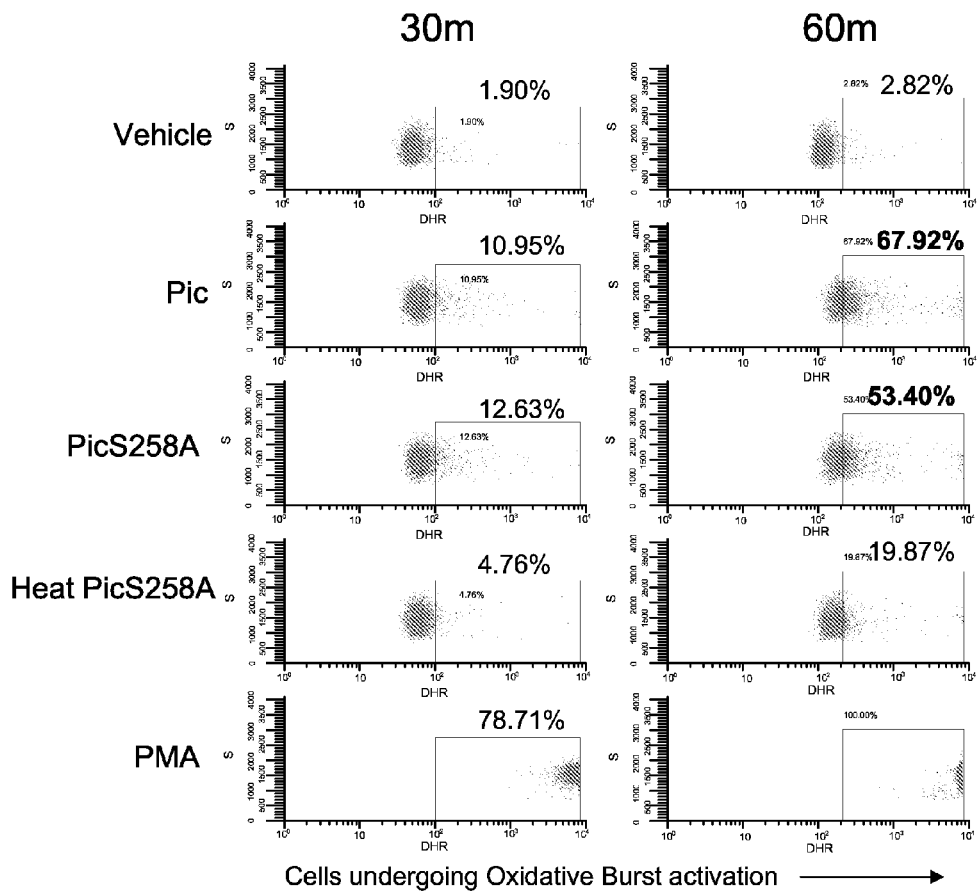
FIG. 16. Activation of neutrophil oxidative burst by Pic. Panel A, 1×10⁶ human neutrophils were labeled with dihydrorhodamine-123 dye for 5 min, immediately treated with 2 µM of LPS-free purified Pic, PicS258A, heat denatured PicS258A or PBS vehicle control, and analyzed by flow cytometry for oxidative burst activation as indicated by FITC fluorescence in 30 and 60 minute time points. 100 ng/ml of PMA was used as a positive control. The cell population was gated to distinguish vehicle-treated and PMA-treated controls. Flow cytometry data are representative of three independent experiments. Panel B, mean and SD of three independent experiments using cells of three volunteers.
Figure 16B:
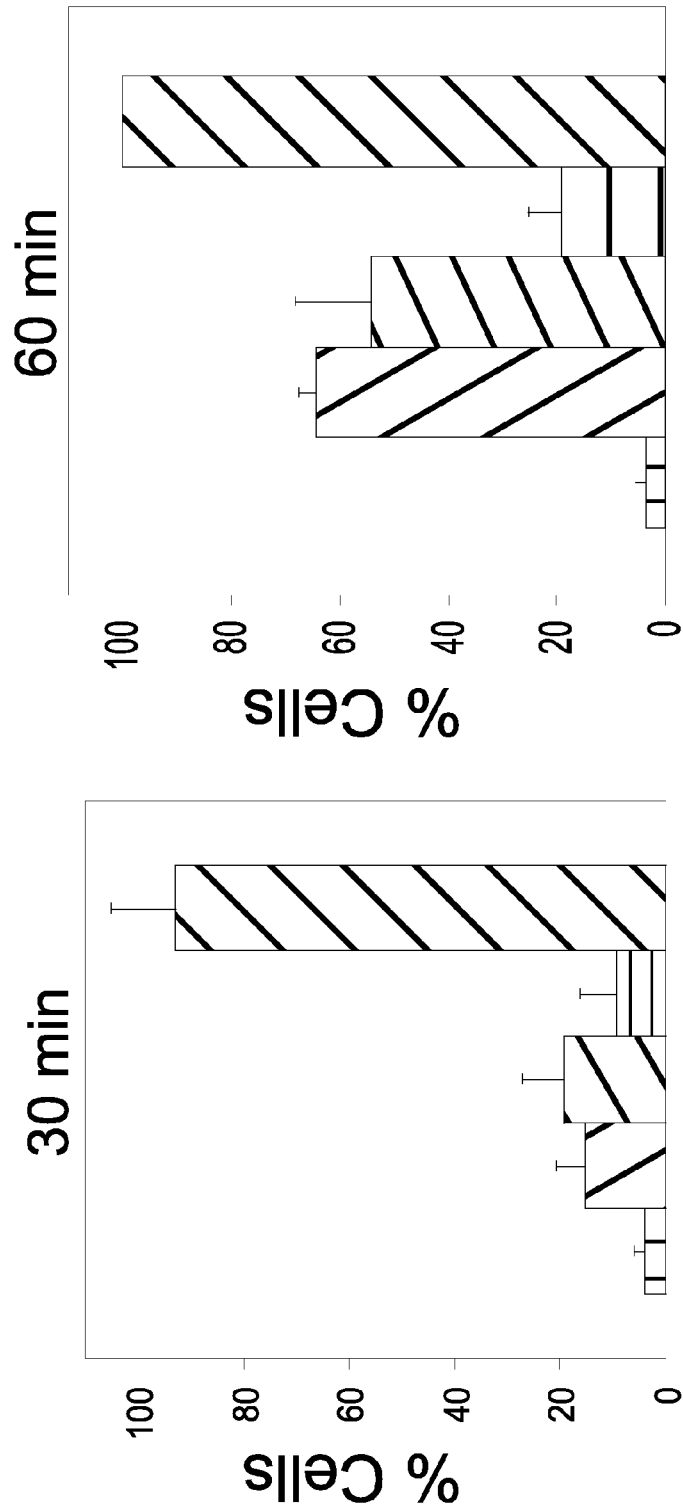

The neutrophil oxidative burst is induced by stimulation of glycoproteins at the leukocyte plasma membrane. It was found that LPS-free Pic at 0.2 µM (the minimal concentration which depleted more than 90% of O-glycoproteins on $10^6$ leukocytes in a 1 h period (see FIG. 21) induced a detectable neutrophil respiratory burst in at least 10-15% of cells after 30 min incubation, and in more than 50% of cells after 60 min (FIG. 16A-B, Pic). Protease mutant PicS258A depleted of bacterial LPS was also able to activate the oxidative burst in neutrophils to the same degree as Pic (FIG. 16A-B), whereas heat-treatment of PicS258A protein reduced significantly its ability to induce the oxidative burst (FIG. 16A-B), further ruling out an effect of contaminating LPS.

Pic Induces Apoptosis of Activated T Cells.

Figure 17:
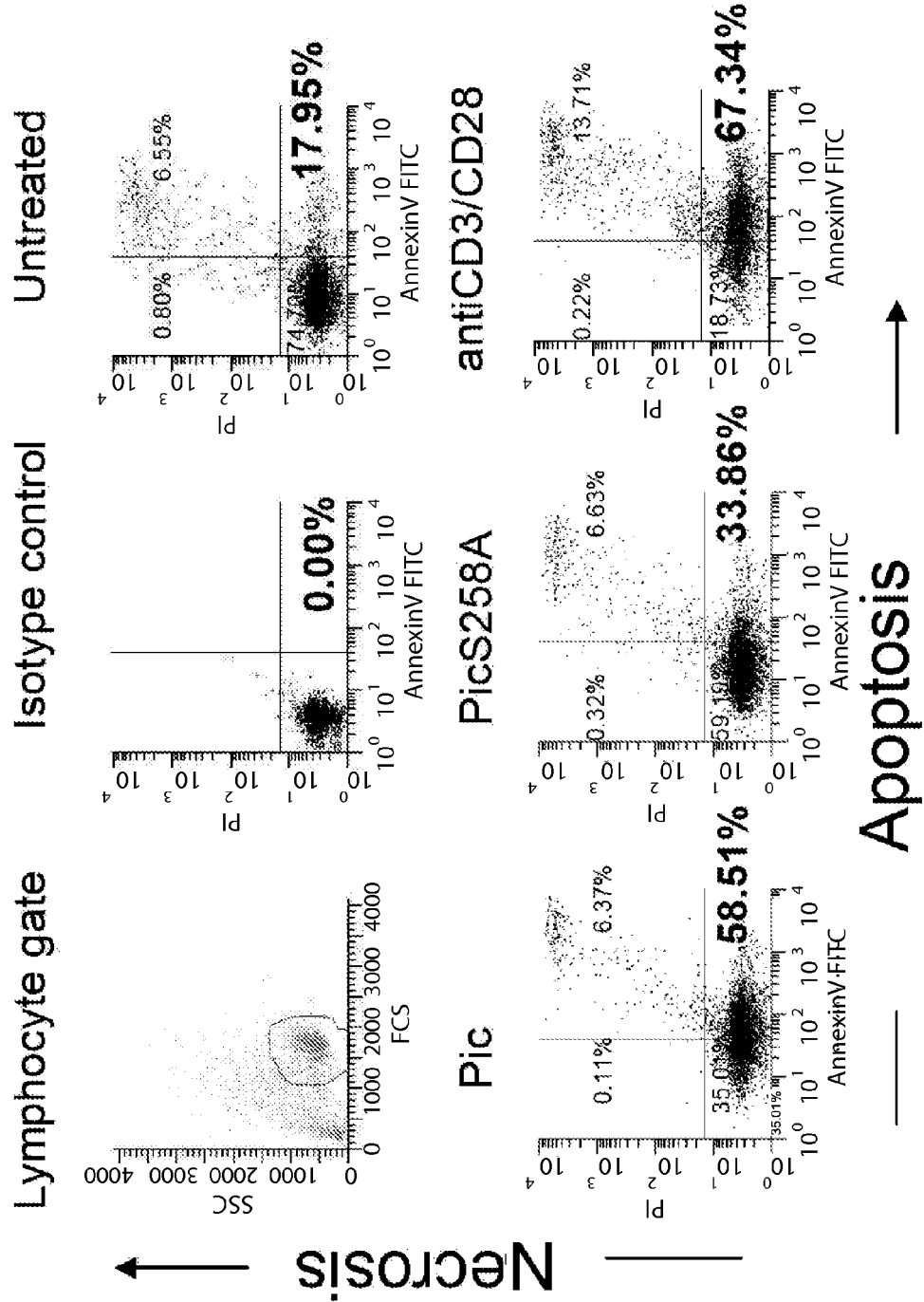
FIG. 17. Pic triggers cell death of activated human T cells. (A) Activated human T cells on day 5 after stimulation with ConA (2 µg/mL) were incubated with 2 µM of purified Pic, PicS258A or control anti-CD3/CD28 antibodies for overnight. Following double staining with annexin-V FITC and propidium iodide (PI), cells were analyzed by flow cytometry to determine the percentage of dead cells. Without gating, 10% of 10 000 total events were displayed. Flow cytometry data is representative of at least two independent experiments.

Many of the O-glycans targeted by Pic are involved in normal T functions as well, including but not limited to adhesion, trafficking, homing and programmed cell death. Various reports have suggested that crosslinking of PSGL-1, CD43, CD44, CD45 and CD99 on activated T cells by specific antibodies or their natural ligands causes programmed cell death (Artus C, Maquarre E, Moubarak R S, Delettre C, Jasmin C, Susin S A, & Robert-Lezenes J (2006) *Oncogene* 25, 5741-5751; Bazil V, Brandt J, Tsukamoto A, & Hoffman R (1995) *Blood* 86, 502-511; Bernard G, Breittmayer J P, de Matteis M, Trampont P, Hofman P, Senik A, & Bernard A (1997) *J Immunol* 158, 2543-2550; Klaus S J, Sidorenko S P, & Clark E A (1996) *J Immunol* 156, 2743-2753.). In order to determine whether Pic binding or cleavage of O-glycans on activated T cells induces apoptosis, we isolated lymphocytes from healthy volunteers and activated the cells with ConA, then treated the cells with Pic; cells were then stained with annexin V or IP, to detect apoptosis or necrosis respectively. Fifty-eight percent of cells treated with Pic underwent apoptosis in these experiments, which was comparable to the levels induced by treatment with anti-CD3 antibodies (FIG. 17). Cells treated with mutant PicS258A exhibited significantly reduced levels of apoptosis, at least two-fold higher than untreated cells (FIG. 17, PicS258A, untreated). Necrosis was also evidenced in all treatments, but exclusively after onset of apoptosis (IP/annexin-V double staining).

Other Class-II SPATEs have Effects Similar to Those of Pic.

Figure 18A:
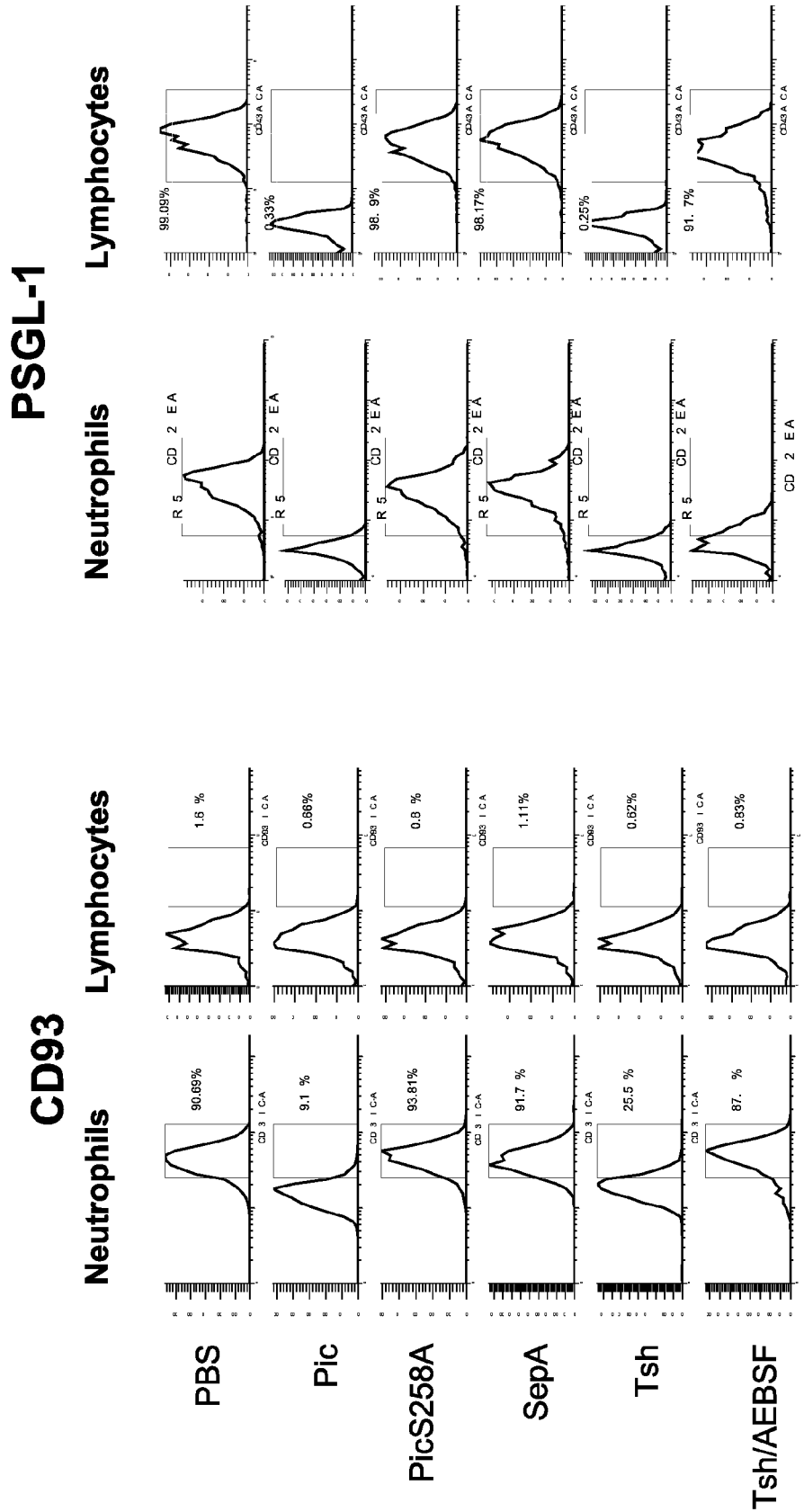
FIG. 18. Tsh degrades the extracellular domain of O-glycosylated mucin-like proteins on human leukocytes. 1×10⁶ PMNs and PBMCs were isolated from human blood and incubated at 37° C. for 30 min. with 1 µM of purified Tsh or Tsh previously inactivated with AEBSF (serine protease inhibitor). 2 µM of Pic, PicS258A and SepA proteins where used as positive and negative controls for digestion. Samples were analyzed by flow cytometry using monoclonal antibodies against the extracellular domain of PSGL-1, CD43, CD93, CD3 and CD16. Lymphocytes were gated by low scatter and using anti CD3, while neutrophils were gated for high scatter and anti-CD 16. Flow cytometry results are representative of at least three independent experiments. Bottom panel, human recombinant fractalkine was treated with purified 2 µM of purified Pic, SepA, Tsh or SigA for 1 h at 37° C. and analyzed by Western blot using a monoclonal antibody against human fractalkine.
Figure 18B:
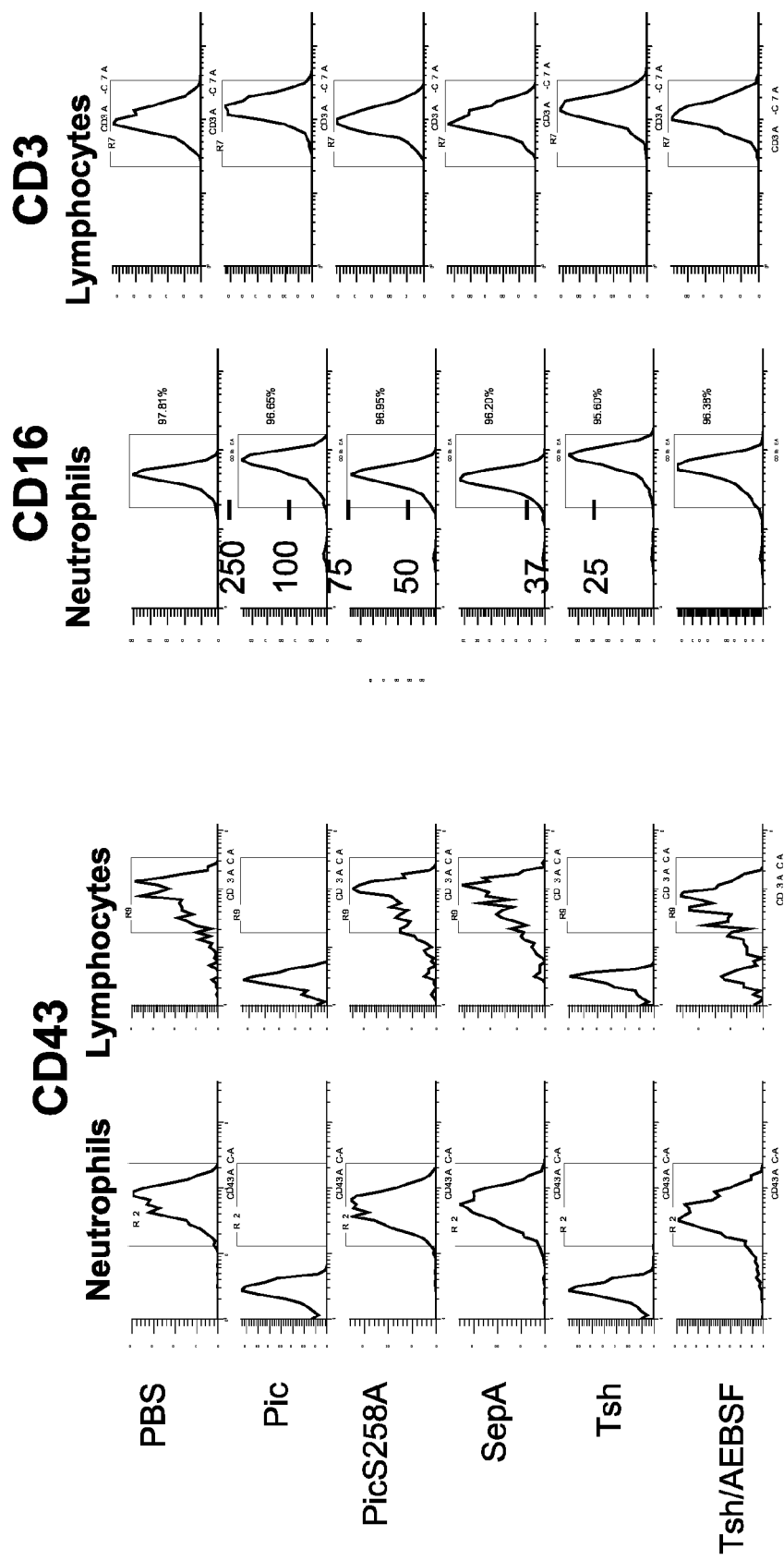
Figure 18C:
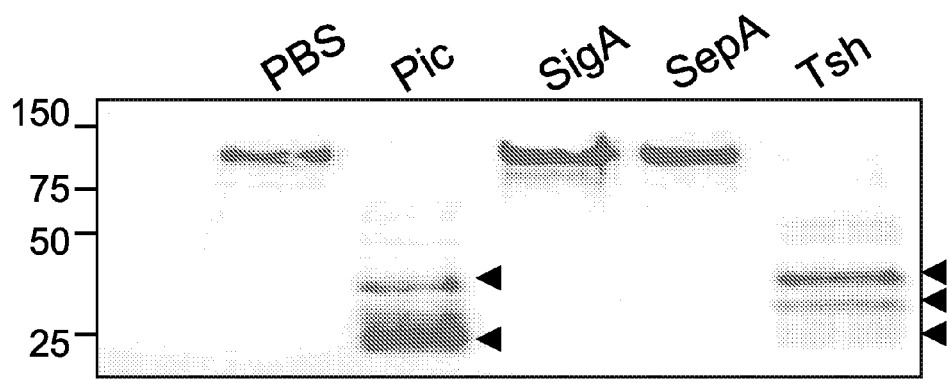

The present inventors have previously classified SPATEs into two subfamilies, Class-1 (cytotoxic) and Class-2 (10), which includes Pic. To determine if other members of the class II SPATES cleave targets similar to those recognized by Pic, the inventors treated human leukocytes with the purified Tsh protein of avian pathogenic *E. coli*, which differs in only two residues from Hbp, found in human invasive *E. coli*. Tsh degraded all leukocyte O-glycans tested, including PSGL-1, CD43, CD93 and fractalkine (FIG. 18), but not other glycans such as MAC-1, selectins or integrins (Data not shown).

Discussion

Pic, a serine protease previously thought to be inefficient at cleaving extracellular mucins (requiring >3 hr to produce demonstrable effect), is in fact highly efficient (~10 min-1 hr) at cleaving leukocyte surface-displayed proteins involved in diverse human immune functions. Pic substrates include a remarkable array of important molecules, all of which are O-linked glycans, and of those tested, with SLeX modification. However, the full range of Pic substrates needs to be further evaluated.

CD43 is one of the most abundant mucin-like leukocyte surface proteins, and is expressed on nearly all lineages of hematopoietic cells, including cells of the bone marrow, the thymus, and peripheral lymphoid tissues (Rosenstein Y, Santana A, & Pedraza-Alva G (1999) *Immunol Res* 20, 89-99.). The role of CD43 is complex but is gradually emerging. In its native form, CD43 prevents leukocytes from adhering to neighboring cells, thereby permitting migration in response to chemokine attraction. Upon processing, the protein plays an opposite role, instead facilitating binding of the leukocyte to neighboring cells (Manjunath N, Johnson R S, Staunton D E, Pasqualini R, & Ardman B (1993) *J Immunol* 151, 1528-1534.; Seveau S, Keller H, Maxfield F R, Piller F, & Halbwachs-Mecarelli L (2000) *Blood* 95, 2462-2470.).

Szabadi et al have recently reported that the StcE protease of enterohemorrhagic *E. coli* inhibits PMN chemoattraction and function by cleavage of CD43 (Szabady R L, Lokuta M A, Walters K B, Huttenlocher A, & Welch R A (2009) *PLoS Pathog* 5, e1000320.). The present data suggest that leukocyte CD43 may also be affected by the pathogens *S. flexneri*, EAEC, UPEC, avian pathogenic *E. coli*, and human invasive *E. coli*, thereby underscoring the pathogenetic importance of this phenomenon in diverse systems (see FIG. 18).

Pic's other targets could be at least as important as CD43. Pic also cleaves PSGL-1/CD162, which is involved in leukocyte trafficking and tethering to endothelial selectins (reviewed in reference (Carlow D A, Gossens K, Naus S, Veerman K M, Seo W, & Ziltener H J (2009) *Immunol Rev* 230, 75-96.)); the multifunctional cell surface glycoprotein CD44, which is involved in cell migration through cell-cell and cell-matrix interactions (Lesley J, Hyman R, & Kincade P W (1993) *Adv Immunol* 54, 271-335; Jalkanen S & Jalkanen M (1992) *J Cell Biol* 116, 817-825;); the CD45 receptor-like protein tyrosine phosphatase (PTP), involved in cell adhesion, migration, modulation of cytokine production and signaling (Harvath L, Balke J A, Christiansen N P, Russell A A, & Skubitz K M (1991) *J Immunol* 146, 949-957; Lai J C, Wlodarska M, Liu D J, Abraham N, & Johnson P J *Immunol* 185, 2059-2070); the CD93 glycoprotein, involved in migration, phagocytosis of antibody and complement opsonized particles (Steinberger P, Szekeres A, Wille S, Stockl J, Selenko N, Prager E, Staffler G, Madic O, Stokinger H, & Knapp W (2002) *J Leukoc Biol* 71, 133-140; Bohlson S S, Zhang M, Ortiz C E, & Tenner A J (2005) *J Leukoc Biol* 77, 80-89.); and fractalkine/CX3CL1, a membrane-bound chemokine that functions not only as a chemoattractant but also as an adhesion molecule, and which is induced on activated endothelial cells by proinflammatory cytokines. These diverse substrates could result in dramatic paralysis of the leukocyte-mediated response at a local level.

In addition to cleavage of glycoproteins involved in cell movement and attraction we were surprised to observe effects of Pic on PMN activation and programmed T cell death. The mechanisms of these effects are not readily apparent from the panel of cleaved substrates, suggesting that still more substrates or as yet uncharacterized mechanisms may be operating. The effects on PMN activation and T cell apoptosis may result from crosslinking of PSGL-1, CD43, CD44, CD45 or CD99 on leukocytes; such cross-linking by specific antibodies or their natural ligands is known to result in activation of the oxidative bust and apoptosis (Chen S C, Huang C C, Chien C L, Jeng C J, Su H T, Chiang E, Liu M R, Wu C H, Chang C N, & Lin R H (2004) *Blood* 104, 3233-3242; Artus C, Maquarre E, Moubarak R S, Delettre C, Jasmin C, Susin S A, & Robert-Lezenes J (2006) *Oncogene* 25, 5741-5751; Bazil V, Brandt J, Tsukamoto A, & Hoffman R (1995) *Blood* 86, 502-511; Bernard G, Breittmayer J P, de Matteis M, Trampont P, Hofman P, Senik A, & Bernard A (1997) *J Immunol* 1158, 2543-2550; Klaus S J, Sidorenko S P, & Clark E A (1996) *J Immunol* 156, 2743-2753).

The mechanism of Pic's substrate specificity is itself interesting. SLeX is a tetrasaccharide carbohydrate that is usually attached to O-glycans, such as PSGL-1, but also found on other glycans, including mucin, CD43 and CD44. This molecule has a vital role in cell-to-cell recognition processes and is a determinant of both E and P selectins. Binding to this particular glycan group provides important functional specificity for Pic, which has apparently exploited the host's use of SLeX as a common inflammatory response signature. The recognition of mucin by Pic via its glycan substitutions has been previously suggested (Gutierrez-Jimenez J, Arciniega I, & Navarro-Garcia F (2008) *Microb Pathog* 45, 115-123.). The inventors found that protease-deficient Pic retains some functions, presumably via non-catalytic substrate binding. Beside the O-glycoproteins tested in this study, CD34, CD68, CD99, CD164 and the recently discovered Tim (T cell immunoglobulin-mucin domain) cluster, a family of proteins harboring mucin-like domains, represent potential targets for Pic and Pic related proteases. The present data suggest that Pic cleaves downstream of O-glycosylated serines or threonines, but additional experiments are needed to elucidate the determinants of Pic cleavage specificity.

Taken together, the many effects of Pic could be highly adaptive to the inflammatory pathogen. Cleavage of the mucin-like glycoproteins would not prevent chemoattraction of leukocytes to areas of infection, but would rather inhibit their anti-bacterial functions once arrived. Thereupon, premature non-specific activation of PMNs would result in enhanced inflammatory effect, including increased tissue damage and increased recruitment of fellow leukocytes to the area. Moreover, apoptosis of T cells by Pic would similarly prolong an aberrant and misdirected inflammatory response, given the central role of T-cell generated IFN-γ in sterilization of *Shigella* infection.

Figure 19:
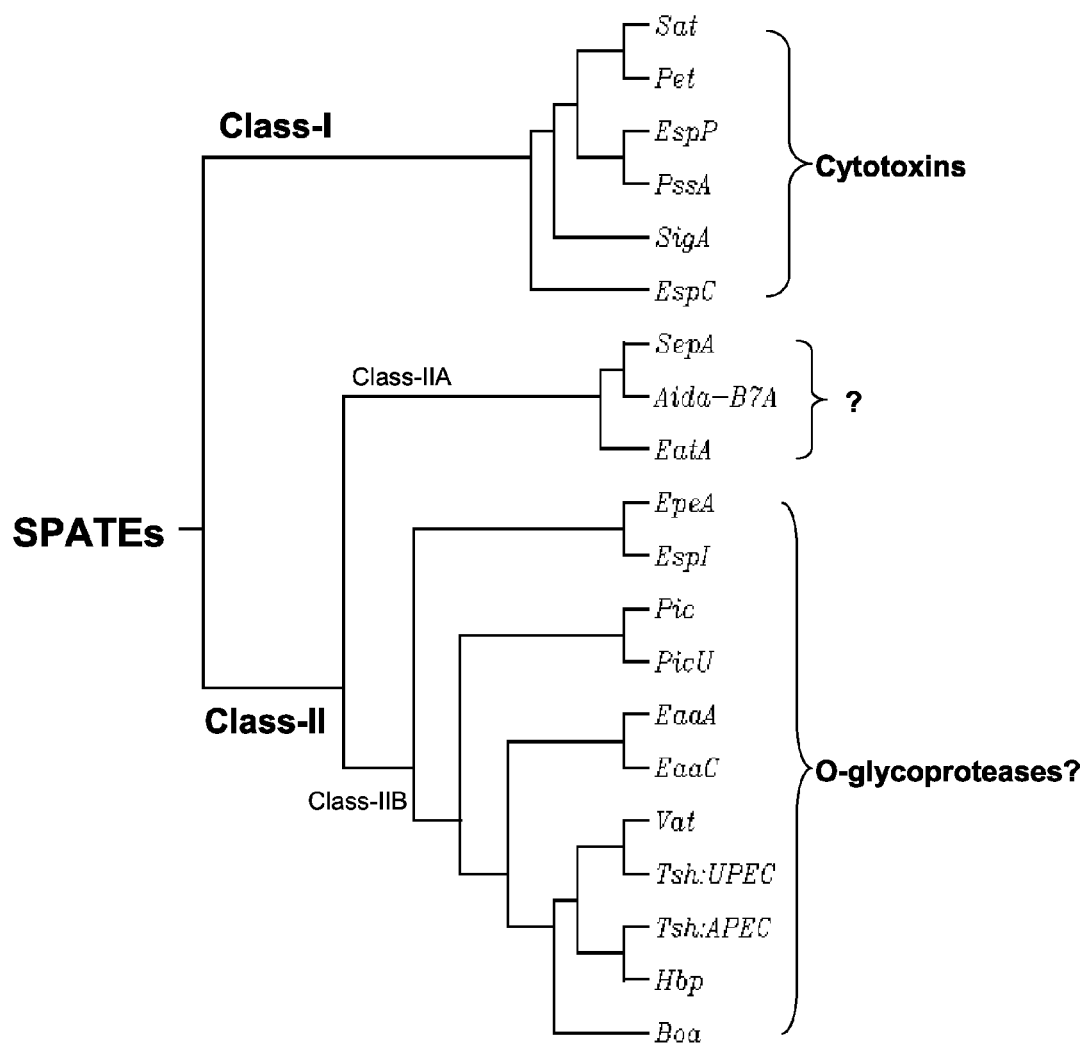
FIG. 19. Phylogenetic analysis of SPATEs reveals two distinct sub-families of the Class-II SPATEs. The aminoacid sequences of SPATE passenger domains were aligned by CLUSTALW (http://align.genome.ip/.). The previously reported Class-II SPATEs can be subdivided into those that do not (Class IIa) and those that do (IIb) cleave SLex glycoproteins.

Despite a plausibly important role for Pic, we note that Pic is only expressed by strains of *Shigella flexneri* 2a (all such strains), which is consistently the dominant *Shigella* serotype worldwide. It is tempting to speculate that Pic may account for this epidemiologic dominance. We also note that Pic-related proteins are produced by other mucosal pathogens (FIG. 19). Interestingly, Pic and Tsh are associated with *Escherichia coli* strains that cause acute pyelonephritis and they are known to be expressed during urinary tract infection, suggesting roles in virulence (Heimer S R, Rasko D A, Lockatell C V, Johnson D E, & Mobley H L (2004) *Infect Immun* 72, 593-597.). Like Pic, Tsh/Hbp cleaves a variety of leukocyte glycans. It is possible that the roles of these related proteases are more finely tuned to the pathogenic strategies of their respective pathogens. The inventors recognize in addition, that the broad functionality of the Pic family of proteases presents therapeutic opportunities against a large number of inflammatory disorders.

Although the present disclosure has been described in example embodiments, additional modifications and variations would be apparent to those skilled in the art.

It is therefore to be understood that the present disclosure herein may be practiced other than as specifically described. Thus, the present embodiments should be considered in all respects as illustrative and not restrictive. Accordingly, it is intended that such changes and modifications fall within the scope of the present disclosure as defined by the claims appended hereto.

REFERENCES

All patents and publications mentioned in this specification are indicative of the level of those skilled in the art to which the invention pertains. All patents and publications herein are incorporated by reference to the same extent as if each individual publication was specifically and individually indicated as having been incorporated by reference in its entirety.

What is claimed is:

1. A method for treating an inflammatory immune response in a patient having an inflammatory bowel disease selected from the group consisting of Crohn's disease, the method comprising administering to said patient a composition comprising Pic protease, which cleaves proteins involved in an inflammatory immune response, after administration to said patient.

2. A method of perturbing immune response in a patient having an inflammatory bowel disease selected from the group consisting of Crohn's disease, the method comprising administering to a patient having a disease or condition in which an active immune response caused by said disease or condition a composition comprising Pic protease, which cleaves proteins involved in the immune response, after administration to said patient.

3. The method of claim 1, wherein administering the composition to the patient by at least one method selected from the group consisting of topical, inhalation, intranasal, oral and intravenous administration.

4. A method for decreasing inflammation in a patient having an inflammatory bowel disease selected from the group consisting of Crohn's disease, the method comprising administering to a patient having inflammation a composition comprising Pic protease, which cleaves proteins involved in an inflammatory immune response, after administration to said patient.

5. The method of claim 4, wherein administering the composition to the patient by at least one method selected from the group consisting of topical, inhalation, intranasal, oral and intravenous administration.

6. The method of claim 4, wherein said composition comprises an aerosolized composition.

7. The method of claim 4, wherein said composition is formulated as a topical composition for topical administration to a patient.

8. The method of claim 4, further comprising administering to the patient at least one additional composition for decreasing inflammation in a patient selected from the group consisting of immunomodulators, antibiotics, biologics.

9. The method of claim 8, further comprising administering to the patient at least one additional composition for decreasing inflammation in a patient selected from the group consisting of aminosalicyclates, corticosteroids, and probiotics.

10. The method of claim 4, wherein said administering comprises direct administration of the Pic protease to a site of action.

* * * * *